US009023400B2

(12) United States Patent
Guimberteau et al.

(10) Patent No.: US 9,023,400 B2
(45) Date of Patent: *May 5, 2015

(54) PROLONGED-RELEASE MULTIMICROPARTICULATE ORAL PHARMACEUTICAL FORM

(75) Inventors: Florence Guimberteau, Montussan (FR); Frederic Dargelas, Pessac (FR)

(73) Assignee: Flamel Technologies, Venissieux (FR)

( * ) Notice: Subject to any disclaimer, the term of this patent is extended or adjusted under 35 U.S.C. 154(b) by 106 days.

This patent is subject to a terminal disclaimer.

(21) Appl. No.: 11/802,610

(22) Filed: May 24, 2007

(65) Prior Publication Data

US 2008/0063725 A1 Mar. 13, 2008

Related U.S. Application Data

(60) Provisional application No. 60/802,795, filed on May 24, 2006.

(51) Int. Cl.
*A61K 31/485* (2006.01)
*A61K 9/20* (2006.01)
*A61K 9/16* (2006.01)
*A61K 9/50* (2006.01)

(52) U.S. Cl.
CPC ............ *A61K 31/485* (2013.01); *A61K 9/5026* (2013.01); *A61K 9/5031* (2013.01); *A61K 9/5042* (2013.01); *A61K 9/1635* (2013.01); *A61K 9/1641* (2013.01); *A61K 9/1652* (2013.01); *A61K 9/2018* (2013.01); *A61K 9/2027* (2013.01); *A61K 9/2031* (2013.01); *A61K 9/2054* (2013.01); *A61K 9/5078* (2013.01)

(58) Field of Classification Search
None
See application file for complete search history.

(56) References Cited

U.S. PATENT DOCUMENTS

| 3,980,766 | A * | 9/1976 | Shaw et al. ................... 514/648 |
| 6,179,862 | B1 * | 1/2001 | Sawhney ....................... 606/214 |
| 6,221,377 | B1 * | 4/2001 | Meyer ............................ 424/434 |
| 2004/0022849 | A1 * | 2/2004 | Castan et al. ................. 424/468 |
| 2004/0126428 | A1 * | 7/2004 | Hughes et al. ................ 424/471 |
| 2005/0214223 | A1 | 9/2005 | Bartholomaeus et al. |
| 2006/0039864 | A1 | 2/2006 | Bartholomaus et al. |
| 2006/0165809 | A1 * | 7/2006 | Guimberteau et al. ....... 424/490 |
| 2008/0020018 | A1 * | 1/2008 | Moodley et al. ............. 424/433 |

FOREIGN PATENT DOCUMENTS

| EP | 0377518 |  | 7/1990 |
| EP | 1293209 | A1 | 3/2003 |
| FR | 2 892 937 |  | 5/2007 |
| FR | 2 897 267 |  | 8/2007 |
| JP | H032114 |  | 1/1991 |
| JP | H11139960 |  | 5/1999 |
| JP | 2002-003366 |  | 1/2002 |
| WO | WO-03/013476 | A1 | 2/2003 |
| WO | WO-03/082204 | A2 | 10/2003 |
| WO | WO 2004/010983 | * | 2/2004 |
| WO | WO-2004/037259 |  | 5/2004 |
| WO | WO-2004/052346 |  | 6/2004 |
| WO | WO-2005/009409 | A2 | 2/2005 |
| WO | WO-2005/079760 | A1 | 9/2005 |
| WO | WO-2006/002886 | A1 | 1/2006 |
| WO | WO-2006/044805 | A2 | 4/2006 |
| WO | WO 2007/054378 |  | 5/2007 |
| WO | WO 2007/093642 |  | 8/2007 |

OTHER PUBLICATIONS

Buri et al., *Formes Pharmaceutiques Nouvelles* [*Novel Pharmaceutical Forms*], Lavoisier 1985, pp. 175-227.

* cited by examiner

*Primary Examiner* — Juliet Switzer
*Assistant Examiner* — Caralynne Helm
(74) *Attorney, Agent, or Firm* — Porzio, Bromberg & Newman P.C.

(57) ABSTRACT

Modified-release multimicroparticulate pharmaceutical form capable of maintaining the modified release of the active principle in an alcoholic solution and of resisting attempts at misuse.

55 Claims, 4 Drawing Sheets

PROLONGED-RELEASE MULTIMICROPARTICULATE ORAL PHARMACEUTICAL FORM

CLAIM FOR PRIORITY

This application claims priority to U.S. Provisional Patent Application Ser. No. 60/802,795, filed May 24, 2006, which is herein incorporated by reference in its entirety.

FIELD OF THE INVENTION

The field of the present invention is that of pharmaceutical forms with modified release of medicinal active principles (APs) intended for oral administration, containing at least one AP, capable of maintaining a modified release of the AP in an alcoholic solution, i.e. not subject to rapid dose dumping in the presence of alcohol; furthermore, they contain anti-misuse means.

The APs considered are pharmaceutical and/or veterinary APs, for example those classified in the category of stupefacients, analgesics or narcotics. Abuse of these APs can give rise to drug addiction-related behavior.

The present invention relates more particularly to the pharmaceutical forms of the type targeted in the paragraph above and comprising a plurality of reservoir microparticles. The present invention relates even more particularly to the pharmaceutical forms for which it is advised not to consume alcohol during administration.

The objective targeted by the present invention is that of improving the multimicroparticulate pharmaceutical forms designed to resist attempts to misuse them, the improvement consisting in preventing the patient from experiencing rapid dose dumping in the presence of a large volume of alcoholic solution.

The invention also relates to a method for preparing the pharmaceutical forms mentioned above.

CONTEXT OF THE INVENTION

The advantage of modified-release pharmaceutical forms for the administration of a drug is well known. They make it possible in particular to ensure more thoroughly that the therapeutic need is covered, because the useful plasma concentration of AP can be maintained for a longer period of time than in the case of immediate-release forms. Furthermore, they make it possible to limit the height and the number of the peaks of plasma concentration of AP, which decreases the toxicity of the drug and/or reduces the side effects thereof. The advantage of modified-release forms is, in this respect, particularly marked for active principles with a narrow therapeutic window. Moreover, these systems make it possible, by virtue of their increased duration of action, to limit the number of daily intakes, which decreases the restrictions on the patient and improves compliance with the treatment.

Systems for prolonging the action of a drug have thus been sought, and the references concerning this objective are numerous. In this regard, the work by Buri, Puisieux, Doelker and Benoit: *Formes Pharmaceutiques Nouvelles [Novel Pharmaceutical Forms]*, Lavoisier 1985, p. 175-227 will be consulted.

However, it appeared that the consumption of alcohol in parallel with the administration of a modified-release (or MR) pharmaceutical form can lead to the accelerated and potentially dangerous release of the AP in the patient. For APs such as opiate-based analgesics, the side effects following too rapid a release of a high dose of AP and the concomitant consumption of alcohol lead to serious consequences which can even sometimes put the patient's vital prognosis in danger.

A modified-release form must therefore ideally be capable of preventing the accidental accelerated release of the AP in an alcoholic solution.

Moreover, a modified-release form must be able to block the intentional misuse of certain active principles such as opiates, which poses a real public health problem.

Intentional misuse is encountered mainly in the case of drug addiction and chemical dependency. In these two cases, individuals who have the intention of misusing an oral solid drug will generally apply themselves to extracting the AP from the modified-release form in order to obtain a rapidly acting product.

The MR pharmaceutical form must obstruct three methods of intentional misuse:
1. inhalation or oral administration of the form previously formulated as an immediate-release powder.
2. Parenteral injection of a small volume of liquid containing the AP extracted from the MR form.
3. Oral administration of a beverage containing the AP in dissolved form.

For cases 2) and 3), the production of a liquid form from a solid oral drug generally involves a step consisting of extraction, in an aqueous or organic phase, of the targeted AP. This extraction is generally preceded by crushing.

Methods of administration 1) by inhalation or 2) by injection are particularly suitable for drug addicts because they are methods which make it possible to accentuate the effects of the AP and which promote its rapid absorption in the body. When the powder obtained by crushing is aspirated via the nose or dissolved in water and injected, the desired effects, drugged feeling or feeling of euphoria, of the AP manifest themselves very rapidly and in an exacerbated manner.

Method 3) also constitutes a particularly serious abuse which affects adolescents and which concerns analgesic APs, more especially morphine and opiate derivatives. Using a highly alcoholic beverage and an opiate analgesic, in particular oxycodone, with a few manipulations, it is possible to extract the opiate analgesic, which can then be absorbed by a drug addict.

The misuse of solid oral drugs can also be observed when, instead of being rapidly swallowed in accordance with the prescription, the drug is chewed before being swallowed, thus bypassing the step of slow disintegration in the stomach and leading to dose dumping.

Thus, in addition to a release profile which makes it possible to prolong and/or to delay the absorption of the AP, an MR release form must make it possible to prevent intentional or unintentional misuse of the AP. In particular, the MR form must simultaneously have the following four essential properties:
a) must not result in an accelerated release of the AP in an alcoholic solution, as might occur, for example, in a patient having accidentally absorbed the drug with an alcoholic drink;
b) must be difficult to crush into the form of an immediate-release powder, in order, for example, to prevent inhalation of the AP;
c) must be difficult to extract in a small volume of liquid, thus preventing parenteral injection of the AP;
d) must not lead to massive solubilization of the AP in a beverage which may or may not be alcoholic, thus preventing oral administration of the AP in an IR form even after a long contact time.

In order to avoid massive dose dumping in the presence of alcohol, which may result in particular from an intentional or unintentional misuse, unpublished application FR 06 50566 describes multimicroparticulate pharmaceutical forms capable of resisting accidental dose dumping in the presence of alcohol, in particular so as to respond to the preoccupations of health professionals faced with accidents caused by this dose dumping in vivo, in patients who have ingested a prolonged-release pharmaceutical form at the same time as a large dose of alcohol. These modified-release forms have the property of maintaining the modified-release of the AP even in a large volume of alcoholic solution (50 to 900 ml). However, these forms are not designed to resist attempts to misuse them, in particular by crushing a dry form, possibly followed by extraction in a liquid medium.

The teaching of this application FR 06 50566 constitutes considerable progress since it proposes a first solution to the problem a) mentioned above. However, it does not propose any solution for problems b), c) and d).

Unpublished application FR 05 53437 describes multimicroparticulate pharmaceutical forms designed so as to be resistant to misuse, in particular intentional misuse. These fraudulent forms of abuse of oral drugs involve various steps (crushing, extraction), and said application describes controlled-release oral forms comprising anti-misuse means:
- the coated microparticles of AP comprise a coating layer which confers resistance to crushing;
- in addition, the pharmaceutical forms of this application contain a viscosity agent which makes it very difficult if not impossible to extract the AP in a liquid medium;
- finally, they optionally contain a quenching agent.

These forms exhibit resistance to extraction in a small volume (for example, 2.5 ml) of an aqueous or alcoholic medium. However, these forms are not suitable for resisting the dose dumping which can occur in the presence of a large volume of alcoholic medium.

Thus, this invention does not propose a technical solution which makes it possible to simultaneously satisfy the four conditions a), b), c) and d) recalled above.

In this context, it must be noted that there exists a need for a modified-release multimicroparticulate pharmaceutical form for the oral administration of AP, capable, firstly, of maintaining the modified release of the AP in an alcoholic solution (unintentional or accidental misuse) and, secondly, of resisting attempts at intentional misuse.

OBJECTIVES OF THE INVENTION

One objective of the invention is to provide novel oral solid drugs which meet the specifications recalled above.

Another objective of the invention is to provide novel oral solid drugs which do not produce a significant acceleration of the release of the AP in an alcoholic solution and have means which make misuse of the AP very difficult or even impossible.

Another objective of the invention is to provide novel oral solid drugs which do not produce a significant acceleration of the release of the AP in an alcoholic solution, the misuse of which, by crushing or after extraction of the AP in a small volume of solvent, will be made difficult or even impossible.

Another objective of the invention is to provide novel oral solid drugs having the following characteristics:
- under normal administration conditions, these oral solid drugs have a therapeutic effect, for example for 12 or 24 hours;
- any attempt at abusive extraction of the AP will result in a non-immediate-release form or in an extracted product which is difficult to use, to such an extent that, after ingestion of the drug, rapid absorption of the AP into the bloodstream will not be possible.

Another objective of the invention is to provide novel oral solid drugs which make it possible to prevent fraudulent abuse of the properties of the AP that it contains, making it difficult to administer the drug orally, nasally and/or by injection (intravenous, subcutaneous, intramuscular, etc.) outside the therapeutic context.

Another objective of the invention is to provide novel oral solid drugs which make it possible to prevent misuse while at the same time guaranteeing for the patient normally followed up, a quality of treatment, in particular a dose, in accordance with said individual's needs.

Another objective of the invention is to provide a method for the manufacture of oral solid drugs which resist immediate AP dose dumping in the presence of alcohol and which comprise anti-misuse means.

DEFINITIONS

For the purpose of the present disclosure of the invention: modified-release form or MR form are synonyms and comprise:
- reservoir systems, i.e. systems in which the release of the AP is controlled by a coating surrounding the AP;
- matrix systems, in which the AP, intimately dispersed in a matrix, for example a polymer-based matrix, is released by diffusion and/or erosion;

"active principle" and the abbreviation "AP" denote both a single active principle or a mixture of several active principles. The AP can be in free form or in the form of a salt, an ester, a hydrate, a solvate, a polymorph, isomers or other pharmaceutically acceptable forms;

the alcohol ingested may come from various alcoholic beverages or drinks such as beer, wine, cocktails, spirits, or mixtures thereof;

in vitro, the term "alcohol", unless otherwise specified, represents ethanol, and the term "alcoholic solution" or "alcoholic medium" represents an aqueous solution of ethanol;

"reservoir microparticles" denotes microparticles comprising AP and individually coated with at least one coating which allows modified release of the AP;

"microparticles of AP" denotes, without distinction, reservoir microparticles and/or microparticles comprising AP which are not necessarily coated;

"microparticles of viscosity agent" denotes microparticles comprising at least one viscosity agent and, optionally, other excipients, with the exclusion of the AP;

"quenching agent" denotes a complexing agent, a deactivating or inactivating agent, a chelating agent, a precipitating agent, or else a scavenger, capable of interacting with an AP and deactivating it;

"microparticles of quenching agent" denotes microparticles comprising at least one quenching agent and, optionally, other excipients, with the exclusion of the AP;

"microparticles" denotes, without distinction, reservoir microparticles, uncoated microparticles of AP, microparticles of AP, microparticles of viscosity agent and microparticles of quenching agent, taken alone or as a mixture;

the in vitro dissolution profiles are realized according to the indications of the European pharmacopoeia (5$^{th}$ edition, §2.9.3) in which the dissolution media conventionally used are described. In order to simulate the gastric medium of an individual having absorbed a large amount of alcohol, the dissolution medium is modified by the addition of ethanol (q.s. for 10% to 40% by volume);

the term "modified release" means that the release of the AP in vitro is such that 75% of the AP is released in a period of time of greater than 0.75 h, and preferably of greater than 1 h, and more preferentially of greater than 1.5 h. A modified-release pharmaceutical form can, for example, comprise an immediate-release phase and a slow-release phase. The modified release can in particular be a prolonged and/or delayed release. Modified-release pharmaceutical forms are well known in this field; see, for example, Remington: *The science and practice of pharmacy*, 19$^{th}$ edition, Mack publishing Co., Pennsylvania, USA;

"immediate release" means that the release is not of modified-release type and denotes the release, by a form, of most of the AP in a relatively brief period of time: at least 75% of the AP is released in 0.75 h, preferably in 30 min;

the similarity between two dissolution profiles is evaluated by means of the similarity factor $f_2$ as defined in the document "Quality of modified-release products" of the European Agency for the evaluation of medicinal products, document referenced CPMP/QWP/604/96 (Annexe 3). An $f_2$ value of between 50 and 100 indicates that the two dissolution profiles are similar;

"agglomerate" or "granule" relates to structures comprising a plurality of microparticles bound to one another by an agent D, optionally comprising other excipients, the diameter of the agglomerates or granules preferably being less than 8000 μm;

the multimicroparticulate oral pharmaceutical forms according to the invention consist of numerous microparticles, whose size is less than a millimeter. The diameters of the microparticles with which the present disclosure is concerned are, unless otherwise indicated, mean diameters by volume. These multimicroparticulate forms can be provided and adapted by those skilled in the art in any of the acceptable pharmaceutical forms, such as tablets, gelatin capsules, sachets, suspensions to be reconstituted;

the term "unit form" is intended to mean the pharmaceutical form which contains one dose of AP which can be in the form, for example, of tablets, gelatin capsules, sachets, suspensions to be reconstituted;

the term "dose dumping" or "rapid dose dumping" is intended to mean an immediate, or significantly accelerated, and unwanted, release of the dose of AP after ingestion per os.

BRIEF DESCRIPTION OF THE INVENTION

In order to attain the objectives that they had set themselves, the inventors have had to find solutions to the various problems listed above and to apply them simultaneously to a single form, since, in order to counter the main methods of misuse, the pharmaceutical form must be both difficult to crush and its AP must be difficult to extract in various solvents and in various volumes.

The pharmaceutical form according to the invention uses harmless and economical physicochemical means (these are compounds which are pharmacologically neutral, approved as excipients by the various pharmacopoeae and registration authorities).

One objective of the present invention is to provide a novel multimicroparticulate form which has the ability to resist dose dumping when it is placed in a large volume of alcohol; furthermore, this form is capable of resisting attempts at intentional misuse (crushing, extraction for injection). The approach which was selected to measure the resistance of the MR pharmaceutical forms to an alcohol-induced dose dumping consists in modifying the conventional tests for dissolution of MR pharmaceutical forms by introducing ethanol into the dissolution medium, for example at a concentration of 10% or of 40% (v/v). The order of magnitude of the final volume is 50 to 900 ml. For a certain number of MR pharmaceutical forms, it is observed that coadministration of said form with alcoholic beverages would lead to an undesired acceleration of the release of the AP(s).

The profile of the desired pharmaceutical form must be adapted to the specifications and depends on the coating of the microparticles. In doing this, it is necessary to avoid ending up with undesired types of behavior, such as:

dissolution profiles which are not controllable, in particular the profile is no longer completely controlled by the coating of the microparticles;

loss of the anti-crushing properties of the microparticles of AP;

dose dumping in the presence of alcohol.

It is to the applicant's credit to have discovered that it is possible, through a judicious choice of excipients, of the proportions thereof and of the methods of using them, to obtain a formulation which corresponds as well as possible to the specifications of the present application.

In other words, the inventors have been able to reconcile the properties conferred by excipients of different nature, in order to obtain, through a judicious choice of the nature of each of these excipients (coating excipient, viscosity modifying excipient, quenching excipient, etc.), of their location (in a microparticle, a binder, a granule, etc.) and of their content, a formulation which corresponds to the initial specifications.

More specifically, the present invention is directed toward an oral pharmaceutical form comprising microparticles of reservoir type, with modified release of at least one AP, not subject to dose dumping in the presence of alcohol, i.e. which resists immediate AP dose dumping in the presence of alcohol, in particular in a large volume and, in addition, the composition and the structure of which make it possible to prevent misuse of the AP this form contains, especially due to anti-misuse means. In particular, the anti-misuse means comprise at least anti-crushing means.

In this pharmaceutical form according to the invention:

the means which prevent AP dose dumping in the presence of alcohol comprise at least one agent D which is a pharmaceutically acceptable compound, the rate of hydration or of solvation or the ability to hydrate or to solvate of which is greater in an aqueous medium free of alcohol than in an alcoholic solution; and at least part of the AP is contained in coated microparticles comprising a coating layer R which ensures the modified release of the AP and which, simultaneously, confers, on the coated microparticles of AP, resistance to crushing, so as to prevent misuse;

and, optionally, at least one viscosity agent V;

and, optionally, at least one quenching agent Q.

In particular, with the oral pharmaceutical form according to the invention, the time for release of 50% of the AP, in an alcoholic solution, is not decreased by more than three-fold compared with the time for release of 50% of the AP measured in an aqueous medium free of alcohol.

The present invention is also directed toward a method for obtaining an oral solid pharmaceutical form which is anti-misuse by crushing and alcoholic extraction.

DETAILED DESCRIPTION OF THE INVENTION

Figure 1:
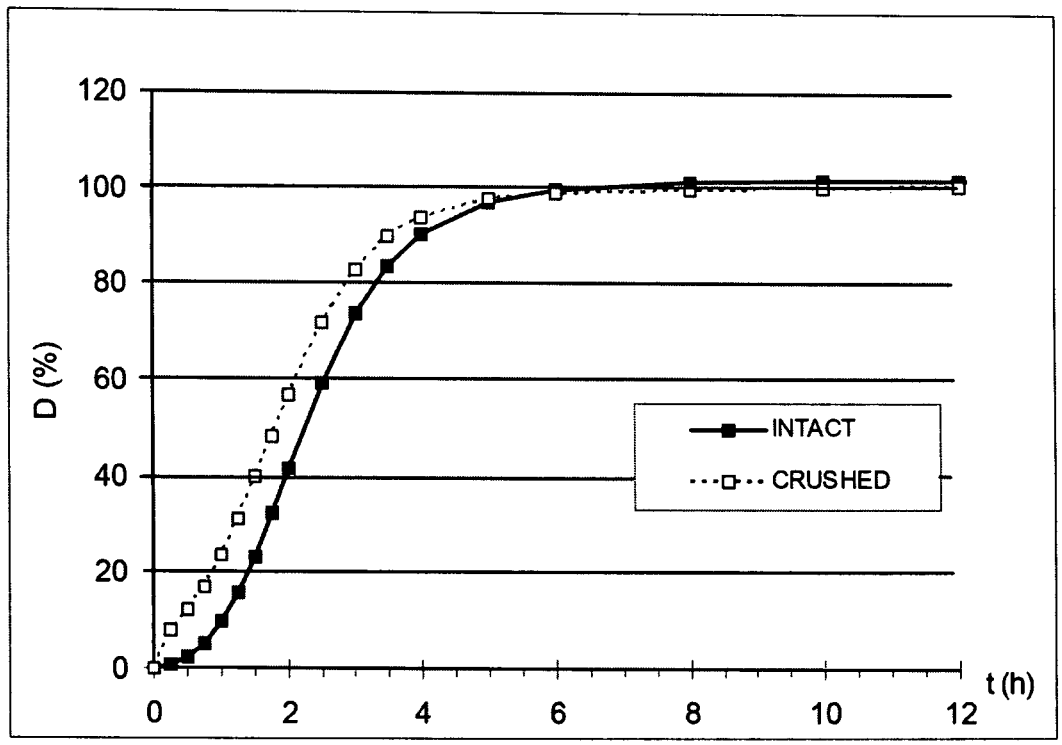
FIG. 1: dissolution of the microparticles prepared in example 3
■: intact □: crushed

The oral pharmaceutical form according to the invention has anti-misuse properties; it comprises microparticles of reservoir type and allows modified release of the AP both in aqueous dissolution media and in alcoholic solutions.

Coated Microparticles of AP

The modified-release coated microparticles of AP are microparticles which are each coated with at least one coating (comprising, for example, at least one polymer) deposited according to the techniques known to those skilled in the art. In this respect, the reference Buri, et al.: *Formes Pharmaceutiques Nouvelles*, Lavoisier 1985, p. 175-227 already mentioned will, for example, be consulted.

The pharmaceutical form according to the invention is multimicroparticulate; it comprises, inter alia, reservoir microparticles with a core comprising the AP coated or film-coated with a coating. This AP core, or microparticle of AP, may be:
- crude (pure) AP in pulverulent form, and/or
- a matrix granule of AP mixed with various other ingredients, and/or
- a supported granule, such as a neutral support, for example of cellulose or of sugar, coated with at least one layer containing AP.

In the case of a matrix granule, the matrix contains the AP and, optionally, other pharmaceutically acceptable excipients, such as binders, surfactants, disintegrating agents, fillers, or pH controllers or modifiers (buffers).

In the case of a supported granule, the layer which contains the AP optionally contains other pharmaceutically acceptable excipients, such as binders, surfactants, disintegrating agents, fillers, or pH controllers or modifiers (buffers). The neutral support can be composed of sucrose and/or of saccharose and/or of dextrose and/or of lactose and/or of a sucrose/starch mixture. The neutral support can also be a cellulose microsphere or any other particle of pharmaceutically acceptable excipient. By way of nonlimiting example of a neutral support, mention may be made of particles of xanthan gum, of guar gum, of calcium phosphate or of calcium carbonate.

Advantageously, the neutral support has a mean diameter of between 1 and 800 µm, and preferably of between 20 and 500 µm.

Coating of the Microparticles of AP

Advantageously, the coated microparticles of AP comprise at least one coating layer R, better still a single coating layer R, which ensures the modified release of the AP and which, simultaneously, confers resistance to crushing on the coated microparticles of AP, in order to prevent misuse.

Even more preferentially, the coating layer R is designed in such a way that it makes it possible, in the event of crushing, to maintain a non-immediate (i.e. modified) release for at least part of the coated microparticles with modified release of AP.

The crushing envisioned here may, for example, be any crushing carried out according to the techniques normally used by perpetrators of misuse, i.e., in particular: pestle/mortar, coffee grinder, crushing between two spoons, biting/chewing, etc.

According to one advantageous embodiment, the coating R is designed in such a way that it makes it possible, in the event of crushing, to maintain a modified release for at least 40%, preferably at least 60%, and even more preferentially at least 80%, of the coated microparticles for modified release of AP.

Preferably, the anti-crushing coating layer R comprises:
- at least one film-forming (co)polymer A1 which is insoluble in the fluids of the digestive tube;
- at least one (co)polymer A2 which is soluble in the fluids of the digestive tube;
- at least one plasticizer A3;
- optionally, at least one surfactant and/or one lubricant and/or one mineral filler and/or one organic filler A4.

In accordance with a purely illustrative and nonlimiting oriented selection of the invention:
A1 is chosen from the group comprising:
  water-insoluble derivatives of cellulose, preferably ethylcellulose and/or cellulose acetate,
  acrylic polymers, for example copolymers of (meth)acrylic acid and of alkyl (for example, methyl)ester, copolymers of an ester of acrylic acid and methacrylic acid bearing at least one quaternary ammonium group (preferably at least one copolymer of alkyl (meth)acrylate and of trimethylammonioethyl methacrylate chloride) and, more specifically, the products sold under the trademarks Eudragit® RS and/or Eudragit® RL,
  poly(vinyl acetate)s,
  and mixtures thereof;
A2 is chosen from the group comprising:
  nitrogenous (co)polymers, preferably from the group comprising polyacrylamides, poly-N-vinylamides, polyvinylpyrrolidones (PVPs) and poly-N-vinyllactams,
  water-soluble derivatives of cellulose,
  polyvinyl alcohols (PVAs),
  polyalkylene oxides, preferably polyethylene oxides (PEOs),
  polyethylene glycols (PEGs),
  and mixtures thereof;
PVP being particularly preferred;
A3 is chosen from the group comprising:
  cetyl alcohol esters,
  glycerol and esters thereof, preferably from the following subgroup: acetylated glycerides, glyceryl monostearate, glyceryl triacetate, glyceryl tributyrate,
  phthalates, preferably from the following subgroup: dibutylphthalate, diethylphthalate, dimethylphthalate, dioctylphthalate, citrates, preferably from the following subgroup: acetyl tributyl citrate, acetyl triethyl citrate, tributyl citrate, triethyl citrate,
sebacates, preferably from the following subgroup: diethyl sebacate, dibutyl sebacate,
adipates,
azelates,
benzoates,
plant oils,
fumarates, preferably diethyl fumarate,
malates, preferably diethyl malate,
oxalates, preferably diethyl oxalate,
succinates, preferably dibutyl succinate,
butyrates,
cetyl alcohol esters,
malonates, preferably diethyl malonate,
castor oil (the latter being particularly preferred),
and mixtures thereof;

A4 is chosen from the group comprising:
anionic surfactants, preferably from the subgroup of alkali metal or alkaline earth metal salts of fatty acids, stearic acid and/or oleic acid being preferred,
and/or nonionic surfactants, preferably from the subgroup of polyoxyethylenated oils, preferably polyoxyethylenated hydrogenated castor oil,
polyoxyethylene/polyoxypropylene copolymers (poloxamer),
polyoxyethylenated sorbitan esters,
polysorbates,
polyoxyethylenated castor oil derivatives,
stearates, preferably calcium stearate, magnesium stearate, aluminum stearate or zinc stearate,
stearyl fumarates, preferably sodium stearyl fumarate,
glycerol behenates,
talc,
colloidal silica,
titanium oxide, magnesium oxide,
bentonite,
microcrystalline cellulose,
kaolin,
aluminum silicate,
and mixtures thereof.

According to a preferred variant of the invention, the coating layer R contains the following components:
A1 is chosen from the group comprising water-insoluble derivatives of cellulose, preferably ethylcellulose and/or cellulose acetate,
A2 is chosen from the group comprising:
nitrogenous (co)polymers, preferably from the group comprising polyacrylamides, poly-N-vinylamides, polyvinylpyrrolidones (PVPs) and poly-N-vinyllactams,
water-soluble derivatives of cellulose,
polyethylene glycols (PEGs),
and mixtures thereof;
A3 is chosen from the group comprising: triethyl citrate, dibutyl sebacate, plant oils, castor oil and mixtures thereof;
A4 is chosen from the group comprising: nonionic surfactants, preferably from the following subgroup:
polyoxyethylenated oils, preferably polyoxyethylenated hydrogenated castor oil,
polyoxyethylene/polyoxypropylene copolymers (poloxamer),
polyoxyethylenated sorbitan esters,
polysorbates,
stearates, preferably magnesium stearate,
and mixtures thereof.

Advantageously, for each constituent A1, A2, A3 and A4 of the coating layer R, its mass m (as % of the total mass A1+A2+A3+A4) bears out
for A1: $10 \leq m \leq 90$, preferably $15 \leq m \leq 80$, and more preferentially $60 \leq m \leq 80$;
for A2: $2 \leq m \leq 50$, preferably $3 \leq m \leq 40$, and more preferentially $5 \leq m \leq 25$;
for A3: $1 \leq m \leq 30$, preferably $2 \leq m \leq 20$, and more preferentially $5 \leq m \leq 15$;
for A4: $0 \leq m \leq 40$, preferably $0 \leq m \leq 30$, and more preferentially $0 \leq m \leq 20$.

Relative to the total mass of the coated microparticles of AP, the coating layer R represents a fraction by mass Tp, expressed as % by weight on a dry basis, such that: $Tp \geq 15$; preferably between 30 and 60, and more preferentially between 40 and 60, and better still between 45 and 55, or approximately 50.

Preferably, the coated microparticles of AP have a volume-average diameter of less than or equal to 1000 μm, preferably of between 50 and 800 μm, and more preferably of between 100 and 600 μm, and better still of between 100 and 400 μm. The diameter of the microparticles is, unless otherwise mentioned, a volume-average diameter.

The techniques used for the manufacture of the microparticles of AP are conventional techniques such as, for example, the fluidized air bed spray coating technique, wet granulation, compacting, extrusion-spheronization.

Agent D

The pharmaceutical form according to the invention comprises at least one agent D which is a pharmaceutically acceptable compound, the rate of hydration or of solvation or the ability to hydrate or to solvate of which is greater in an aqueous medium free of alcohol than in an alcoholic solution. It may be:
a composition with a higher solubilization rate in water than in an alcoholic solution;
a compound which is soluble in water and insoluble in an alcoholic solution;
or a compound which is insoluble in water or in an alcoholic solution, and which swells more or more rapidly in water than in an alcoholic solution.

Preferably, the agent D is chosen from the group of following products:
cellulose derivatives such as, for example:
methylcellulose,
(hydroxy)(alkyl)celluloses, (for example, hydroxypropylcellulose, hydroxypropylmethylcellulose, hydroxyethylcellulose),
carboxyalkylcelluloses (for example, carboxymethylcellulose) and salts thereof,
celluloses (powder or microcrystalline),
crosslinked carboxyalkylcelluloses:
crosslinked carboxymethylcelluloses (for example, sodium croscarmellose),
polyalkylene oxides (for example, polyethylene oxide or polypropylene oxide),
polysaccharides, for example:
natural starches (for example, of maize, wheat or potato) or modified starches (for example, modified with sodium glycolate),
alginates and salts thereof such as sodium alginate,
polacrilin potassium,
guar gums,
carrageenans,
pullulans, pectins,
chitosans and derivatives thereof,
and mixtures thereof,
proteins, for example:
gelatin,
albumins,
casein,
lactoglobulins,
and mixtures thereof,
clays, such as bentonite, laponite and mixtures thereof.
Even more preferably, the agent D is chosen from the group of following products:
hydroxyalkylcelluloses (for example, hydroxypropylcellulose, hydroxypropylmethylcellulose, hydroxyethylcellulose),
methylcellulose,
carboxy(alkyl)celluloses and salts thereof,
guar gums,
carrageenans,
and mixtures thereof.

The agent D can be incorporated in various ways, optionally combined with one another, into the pharmaceutical form according to the invention. It may be one of the constituents:
of the core of AP (or uncoated microparticle of AP):
in the neutral support of the microparticles and/or
in the layer containing the AP and deposited onto the neutral support of the microparticles and/or
in the granule containing the AP; and/or
of the coating of the microparticles; and/or
of a mixture with the microparticles:
either in the binding phase of granules, pellets, tablets including the microparticles of AP and/or
or in a different type of microparticles and/or
or in a different type of granules; and/or
one of the outer constituents of a monolithic form (for example, constituent of a gelatin capsule, coating of a tablet or of a gelatin capsule).

According to a first embodiment of the invention, the agent D is present in the core of AP, or uncoated microparticle of AP. Preferably, the agent D is present in the core of the microparticles in a proportion of 5% to 70%, preferably of 15% to 60%, of the total mass of the core of AP.

According to a second embodiment of the invention, the agent D is included in the coating of the microparticles. In this case, the agent D can constitute, on its own, a coating layer inside or outside the coating controlling the diffusion. It can also be mixed with the constituents A1, A2, A3 and, optionally, A4 of the coating which controls the modified release of the AP. Preferably, the agent D is present in the coating in a proportion of 3% to 30%, preferably of 10% to 20%, of the total mass of the coating. Preferably, the following compounds are chosen: the polymer A1 is ethylcellulose, the polymer A2 is PVP, the plasticizer A3 is castor oil, A4 is a poloxamer, and the agent D is chosen from guar gum, hydroxyethylcellulose, methylcellulose, hydroxypropylmethylcellulose and sodium carboxymethylcellulose, and mixtures thereof.

According to a third embodiment, the agent D is included in the binding phase of granules or of pellets or else of tablets including the microparticles of AP.

The granules, pellets or tablets are obtained by the techniques known to those skilled in the art, such as, for example, granulation, extrusion or compression. The agent D is present as a mixture with the microparticles, in a proportion of 0.5% to 30% w/w, preferably of 0.5% to 25% w/w, and even more preferentially of 1% to 20% w/w, of the total mass of the mixture.

According to a fourth embodiment, the agent D is at least partly in the form of microparticles or, preferably, of granules distinct from those which contain the AP. For example, the coated microparticles of AP are granulated according to conventional techniques, and granules of the same size and of the same density, of agent D, are prepared separately, which granules can also contain a viscosity agent and/or a quenching agent (see below).

According to a fifth embodiment, the agent D is one of the components of the material constituting the gelatin capsule which contains the microparticles.

According to a sixth embodiment, the agent D is included in a coating deposited onto the gelatin capsule containing the microparticles or onto the tablet containing the microparticles. For example, the gelatin capsule is gelatin-based, and the coating contains sodium carboxymethylcellulose and/or hydroxyethylcellulose as agent D, preferably in a proportion of 25% w/w of agent D relative to the mass of the empty gelatin capsules.

In the case of the fifth and sixth embodiments, a finishing layer may be deposited onto the gelatin capsule or the tablet.

The various embodiments, as regards the agent D, can be combined with one another. In such a case, it is entirely possible to envision incorporating various agents D for each of the embodiments indicated.

Viscosity Agent V

The viscosity agent V is chosen from viscosity agents which are soluble in at least one of the following solvents: water, alcohols, ketones, and mixtures thereof, this or these agent(s) being capable of increasing the viscosity of the extraction solvent so as to counteract misuse, in particular by injection. The term "water" is here intended to mean any aqueous solvent, such as water, stricto sensu, or any aqueous solution, for example of organic acid (for example, acetic acid), saline solutions, sodas or beverages. The term "alcohols" is here intended to mean all alcohols taken by themselves or as a mixture with one another, and the term "ketones" is intended to mean all ketones taken by themselves or as a mixture with one another.

Preferably, the viscosity agent V is chosen from the following groups of polymers:
poly(meth)acrylic acids and derivatives thereof, and/or
polyalkylene glycols (for example, polyethylene glycol), and/or
polyalkylene oxides (for example, polyethylene oxide), and/or
polyvinylpyrrolidones, and/or
gelatins, and/or
polysaccharides, preferably from the subgroup comprising: sodium alginate, pectins, guars, xanthans, carrageenans, gellans and cellulose derivatives (in particular, hydroxypropylmethylcellulose, methylcellulose, hydroxyethylcellulose, hydroxypropylcellulose, carboxymethylcellulose),
and mixtures thereof.

Advantageously, according to a preferred variant of the invention, the viscosity agent V is chosen from:
polyalkylene oxides (for example, polyethylene oxide), and/or
xanthans, and/or
cellulose derivatives (in particular, hydroxypropylcellulose),
and mixtures thereof.

According to one mode of the invention, the viscosity agent V is a polyethylene oxide having a high molecular weight, for example having a molecular weight of 1 million g/mol to 8 million g/mol, for example 2 million, 5 million or 7 million g/mol.

According to a preferred mode, the viscosity agent V is capable of increasing the viscosity of the liquid used for the possible extraction, so as to trap the AP extracted in the viscous medium. This agent V makes it possible to increase the viscosity of the extraction liquid, for example above 100 mPa·s, preferably 200 mPa·s, and even more preferentially above 500 mPa·s, and better still 1000 mPa·s.

According to one variant of the invention, the viscosity agent V is effective in the case of both an extraction in an aqueous phase or an organic phase; for example, the agent V is a mixture of hydrophilic and hydrophobic compounds, so as to ensure a high viscosity of the extraction liquid (for example ≥100 mPa·s), whether the latter is aqueous or organic.

The amount of agent V is adjusted so as to render the viscosity of 2.5 ml of extraction liquid greater than or equal to 100 mPa·s.

According to several variants, in the pharmaceutical form according to the invention, at least one viscosity agent V is present:
  in and/or on microparticles,
  and/or in the free state, i.e. not contained in, or supported by, microparticles.

Advantageously, the viscosity agent is mainly in the form of microparticles distinct from the microparticles of AP. When the pharmaceutical form is a divided form (gelatin capsule, sachet, suspension to be reconstituted), the microparticles of viscosity agent have a density and a particle size comparable to those of the microparticles of AP. For example, the microparticles of viscosity agent V and the microparticles of AP have a similar size distribution and a similar density. Thus, they cannot be separated from the microparticles of AP, in particular by conventional means such as sifting or centrifugation.

When the pharmaceutical form according to the invention comprises granules containing, firstly, microparticles of AP and, secondly, granules containing viscosity agent V, optionally combined with the agent D, it is preferable for said granules to have a similar size distribution, a similar density, a similar shape and a similar color. Thus, the granules comprising the viscosity agent and/or the agent D are physically indistinguishable from the granules of AP, in order to obstruct the sorting thereof by any appropriate physical means.

Quenching Agent Q

When the multimicroparticulate pharmaceutical form comprises at least one salt of an active principle, or an active principle bearing a function ionizable in solution, a preferred embodiment of the invention consists in adding to said pharmaceutical form at least one quenching agent Q. The latter is chosen such that, during an attempt at extraction, it forms, with the AP, in an aqueous or aqueous-alcoholic solution, a poorly soluble complex.

For the purpose of the present invention, a quenching agent Q is an agent present in the pharmaceutical form in a free form, i.e. a noncomplexed form. The term "noncomplexed" signifies that there is no complex or chemical interaction between the quenching agent Q and the salt of active principle AP in the solid pharmaceutical form.

When the salt of AP and the quenching agent Q are simultaneously in a solvent, for example in the case of an illicit attempt to extract the AP, the quenching agent Q is capable of inducing a complexation or a chemical interaction with the salt of AP in said solvent. For the purpose of the present invention, the quenching agent Q is considered to be "capable of inducing a complexation" with the salt of AP when the quenching agent Q is capable of inducing complexation of the salt of AP in at least one usual solvent chosen from water and aqueous solutions, such as water-ethanol mixtures, alcohol, alcoholic beverages, sodas, vinegar, aqueous hydrogen peroxide solution, and mixtures thereof. Advantageously, the quenching agent Q is capable of inducing complexation of the salt of AP in more than one of these usual solvents.

The quenching agents Q used to trap the AP, in particular analgesic, are harmless, including for a regular use. These are pharmacologically inert products approved by the various pharmacopoeia and authorities for registering drugs.

In one pharmaceutical form according to the invention, least one quenching agent Q is present:
  in microparticles free of AP, and/or on microparticles, and/or
  in the free state, i.e. not contained in, or supported by, microparticles.

Preferably, in a pharmaceutical form according to the invention, the quenching agent Q is present in a first phase separate from at least a second phase, said second phase containing at least one salt of AP. For example, the pharmaceutical form comprises microparticles of salt of AP and microparticles of quenching agent Q which are distinct. Advantageously, said microparticles have a similar size distribution and a similar density, and are impossible to separate from one another by sifting.

Preferably, the quenching agent Q comprises a salt, which contains ions capable of forming a complex with the AP in solution. These ions are preferably organic ions of polarity opposite to that of the AP in solution: if, in solution, the AP is in anionic form, the quenching agent Q comprises an organic cation, a metal cation, or a mixture thereof. Similarly, when the AP in solution is in cationic form, the quenching agent Q comprises an organic anion.

For example, mention may be made of the following salts which have an organic anion:
  anionic organic salts, such as sodium dodecyl sulfate or sodium docusate;
  anionic polymers, such as (meth)acrylic copolymers (for example, Eudragit® S and Eudragit® L), crosslinked polyacrylic acids (for example, Carbopol), carboxymethylcellulose and its derivatives, crosslinked carboxymethylcellulose and its derivatives and other polysaccharides (for example, alginate, xanthan gum or gum arabic), alginate (sulfonate) propylene glycol;
  monovalent or polyvalent salts, such as glucuronates, citrates, acetates, carbonates, gluconates, succinates, phosphates, glycerophosphates, lactates, trisilicates, fumarates, adipates, benzoates, salicylates, tartrates, sulfonamides, acesulfames;
  saponified fatty acids, such as salts of acetic acid, succinic acid, citric acid, stearic acid, palmitic acid, and self-emulsifying glyceryl monooleates;
  polyamino acids, proteins or peptides, such as albumins, caseins, globulins and enzymes;
  and mixtures thereof.

In another embodiment, the ion of polarity opposite to that of the AP in solution is a metal cation, an organic cation, or a mixture thereof. For example, mention will be made of the following salts which contain an organic or metal cation:
  cationic salts, for example of the metals Ca, Fe, Mg or Zn, in the form of acesulfames, acetates, adipates, benzoates, carbonates, chlorides, citrates, fluorides, fumarates, gluconates, glucuronates, glycerophosphates, hydroxides, iodates, iodides, lactates, oxides, phosphates, trisilicates, phosphates, salicylates, succinates, sulfonamides, tartrates;

organic cationic salts, such as quaternary ammonium salts, in particular trimethyltetradecylammonium bromide or benzethonium chloride;

cationic polymers, such as chitosan and (meth)acrylic copolymers (for example, Eudragit® RS, Eudragit® RL or Eudragit® E);

polyamino acids, proteins or peptides;

and mixtures thereof.

The quenching agent Q may be an ion exchange resin, preferably a strongly acidic cation exchange resin when the AP is cationic or a strongly basic anion exchange resin when the AP is anionic. Advantageously, such an ion exchange resin is contained in a first phase distinct from a second phase which contains the AP.

In one embodiment of the invention, the ion exchange resin will, for example, be a derivative of a styrene/divinylbenzene copolymer.

In one embodiment of the invention, the strongly acidic cation exchange resin will, for example, be a derivative of a sulfonic styrene/divinylbenzene copolymer, such as Amberlite® IRP69, Amberlite® IR69F (Rohm and Haas); Amberlite 200, Amberlite 200C (Rohm and Haas), or Dowex 88 (Dow), and the like.

In one embodiment of the invention, the strongly basic anion exchange resin will, for example, be chosen from derivatives of styrene/divinylbenzene copolymers bearing quaternary ammonium functions, such as Duolite® AP143 (Rohm and Haas), Amberlite® IRA958, Amberlite IRP67 (Rohm and Haas) and Dowex 22 (Dow).

The quenching agent Q in the form of resin can also be chosen from crosslinked copolymers of methacrylic acid and of divinylbenzene or a salt thereof, such as Amberlite® IRP88 and Amberlite® IRP64 (Rohm and Haas), and Dowex MAC-3 (Dow).

The quenching agent Q in the form of ion exchange resin can also be chosen from phenolic polyamines, such as Amberlite® IRP58 (Rohm and Haas).

Mixtures of these various resins can also be envisioned.

According to one embodiment of the invention, the quenching agent Q in the form of ion exchange resin is in a first phase separate from at least a second phase, said second phase comprising the salt of AP. For example, the quenching agent Q in the form of ion exchange resin is contained in microparticles distinct from the microparticles comprising the salt of AP. The microparticles of AP and the microparticles of quenching agent Q in the form of ion exchange resin can be in a form such that they have a similar size distribution and a similar density and such that they cannot be separated by sifting.

In a first preferred embodiment of the invention, the quenching agent Q is chosen from:

anionic organic salts, such as sodium dodecyl sulfate or sodium docusate;

cationic organic salts, such as quaternary ammonium salts, in particular trimethyltetradecylammonium bromide or benzethonium chloride;

strongly acidic cation exchange resins or strongly basic anion exchange resins, depending on the polarity of the AP.

In a second preferred embodiment of the invention, the quenching agent Q is chosen from:

strongly acidic cation exchange resins: Amberlite® IRP69, Amberlite® IR69F (Rohm and Haas); Amberlite® 200, Amberlite 200C (Rohm and Haas), or Dowex 88 (Dow), and mixtures thereof, when the AP is cationic;

strongly basic anion exchange resins: Duolite® AP143 (Rohm and Haas), Amberlite® IRA958, Amberlite® IRP67 (Rohm and Haas), and Dowex 22 (Dow), and mixtures thereof, when the AP is anionic.

The amount of agent Q is adjusted by those skilled in the art by calculating the amount of ionic charge required to trap all or part of the dose of AP contained in the unit form. The amount of quenching agent Q must be such that it makes it possible to complex sufficient AP so that the remaining amount of AP free in solution is insufficient to achieve the desired effect, in the case of illicit use. Preferably, the amount of quenching agent Q is sufficient to complex all the AP of the unit dose.

Excipient in the Free State

The pharmaceutical form can optionally contain one or more pharmaceutically acceptable excipients, in the free state, i.e. not contained in or supported by microparticles of AP, said excipient contributing to the resistance of the coated microparticles of AP to crushing.

Preferably, these excipients which contribute to the resistance to crushing of the coated microparticles of AP are chosen from the group comprising:

calcium stearate;
glyceryl palmitostearate;
magnesium oxide;
polyalkylene glycols, for example polyethylene glycols;
polyvinyl alcohol;
sodium benzoate;
stearic acid;
corn starch;
talc;
colloidal silica;
zinc/magnesium stearate;
stearyl fumarate;
and mixtures thereof.

Description of the Pharmaceutical Form

Preferably, with the oral pharmaceutical form according to the invention, for modified release of at least one AP both in aqueous dissolution media and in alcoholic solutions, the time for release of 50% of the AP in an alcoholic solution:

is not decreased by more than three-fold compared with the time for release of 50% of the AP measured in an aqueous medium free of alcohol;

is preferably not decreased by more than two-fold compared with the time for release of 50% of the AP measured in an aqueous medium free of alcohol;

is preferably not decreased by more than 1.5-fold compared with the time for release of 50% of the AP measured in an aqueous medium free of alcohol;

is preferably similar to that measured in an aqueous medium, according to the similarity factor $f_2$ defined above;

or even the time for release of 50% of the AP in an alcoholic solution is greater than the time for release of 50% of the AP in an aqueous medium free of alcohol.

In general, the pharmaceutical form according to the invention comprises:

a) an AP, at least part of which is contained in microparticles individually coated with a coating R which ensures the modified release of the AP and simultaneously confers resistance to crushing of the coated microparticles of AP. The constituents A1, A2, A3 and A4 of the coating layer R meet, in terms of percentage by mass relative to the total mass A1+A2+A3+A4, the requirements mentioned above;

b) at least one agent D which is present in a proportion of 0.5% to 30% w/w, preferably of 0.5% to 25% w/w, and even more preferentially of 1% to 20% w/w, of the total mass of the unit form;
c) optionally, at least one viscosity agent V present in a proportion of 2 to 400 mg, preferably of 5 to 200 mg, and even more preferentially of 10 to 100 mg per unit form;
d) optionally, at least one quenching agent Q, the amount of which is adjusted in order to trap all or part of the dose of AP contained in the unit form.

According to a preferred mode, the quenching agent Q is included in a phase or in microparticles separate from the microparticles of AP.

Preferably, the viscosity agent V is contained in microparticles distinct from the microparticles of AP. Advantageously, the pharmaceutical form according to the invention comprises microparticles of viscosity agent V and microparticles of AP, said microparticles having a similar size distribution and a similar density and being impossible to separate from one another by sifting.

According to an embodiment 1 of the invention, the coating layer R contains the following components:
A1 is chosen from the group comprising water-insoluble derivatives of cellulose, preferably ethylcellulose and/or cellulose acetate,
A2 is chosen from the group comprising:
nitrogenous (co)polymers, preferably from the group comprising polyacrylamides, poly-N-vinylamides, polyvinylpyrrolidones (PVPs) and poly-N-vinyllactams,
water-soluble derivatives of cellulose,
polyethylene glycols (PEGs),
and mixtures thereof;
A3 is chosen from the group comprising: triethyl citrate, dibutyl sebacate, plant oils, castor oil, and mixtures thereof;
A4 is chosen from the group comprising: nonionic surfactants, preferably from the following subgroup:
polyoxyethylenated oils, preferably polyoxyethylenated hydrogenated castor oil,
polyethylene oxide-polypropylene oxide copolymers (poloxamer),
polyoxyethylenated sorbitan esters,
polysorbates,
stearates, preferably magnesium stearate,
and mixtures thereof.

According to an embodiment 2 of the invention, the agent D is chosen from the group of following products:
hydroxyalkylcelluloses (for example, hydroxypropylcellulose, hydroxypropylmethylcellulose, hydroxyethylcellulose),
methylcellulose,
carboxy(alkyl)celluloses, and salts thereof,
guar gums,
carrageenans,
and mixtures thereof.

According to an embodiment 3 of the invention, the viscosity agent V is chosen from:
polyalkylene oxides (for example, polyethylene oxide), and/or
xanthans, and/or
cellulose derivatives (in particular, hydroxypropylcellulose),
and mixtures thereof.

According to a variant of embodiment 3 of the invention, the viscosity agent V is a polyethylene oxide having a high molecular weight, for example having a molecular weight of 1 million g/mol to 8 million g/mol, for example 2 million, 5 million or 7 million g/mol.

According to an embodiment 4 of the invention, the quenching agent Q is chosen from:
anionic organic salts, such as sodium dodecyl sulfate or sodium docusate;
cationic organic salts, such as quaternary ammonium salts, in particular trimethyltetradecylammonium bromide or benzethonium chloride;
ion exchange resins, preferably a strongly acidic cation exchange resin or a strongly basic anion exchange resin.

According to an embodiment 5 of the invention, the quenching agent Q is chosen from:
strongly acidic cation exchange resins: Amberlite® IRP69, Amberlite® IR69F (Rohm and Haas); Amberlite 200, Amberlite 200C (Rohm and Haas), or Dowex 88 (Dow), and mixtures thereof, when the AP is cationic;
strongly basic anion exchange resins Duolite® AP143 (Rohm and Haas), Amberlite IRA958, Amberlite IRP67 (Rohm and Haas) and Dowex 22 (Dow), and mixtures thereof, when the AP is anionic.

These embodiments 1 to 5 of the invention can be combined with one another. In particular, a pharmaceutical form according to the invention simultaneously comprises the coating layer R and the agent D of embodiments 1 and 2. According to a preferred variant, the pharmaceutical form also comprises at least one viscosity agent V according to embodiment 3. Finally, the pharmaceutical form can contain a quenching agent Q according to embodiment 4 or 5.

Of course, the final pharmaceutical form according to the invention may be optimized by the addition of other conventional ingredients known to those skilled in the art, such as, in particular, colorants, pigments, preserving agents, aromas, and mixtures thereof.

According to a preferred embodiment 6, the unit pharmaceutical form according to the invention is a tablet, comprising:
a) an AP, at least part of which is contained in microparticles individually coated with a coating R which ensures the modified release of the AP and simultaneously confers resistance to crushing of the coated microparticles of AP.

For each constituent A1, A2, A3 and A4 of the coating layer R, its mass m (as % of the total mass A1+A2+A3+A4) bears out:
for A1: $10 \leq m \leq 90$, preferably $15 \leq m \leq 80$, and more preferentially $60 \leq m \leq 80$;
for A2: $2 \leq m \leq 50$, preferably $3 \leq m \leq 40$, and more preferentially $5 \leq m \leq 25$;
for A3: $1 \leq m \leq 30$, preferably $2 \leq m \leq 20$, and more preferentially $5 \leq m \leq 15$;
for A4: $0 \leq m \leq 40$, preferably $0 \leq m \leq 30$, and more preferentially $0 \leq m \leq 20$;
b) at least one agent D is present as a mixture with the microparticles in a proportion of 1% to 30% w/w, preferably of 2% to 25% w/w, and even more preferentially of 2% to 20% w/w, of the total mass of the unit form;
c) at least one viscosity agent V is contained in microparticles distinct from the microparticles of AP. The viscosity agent V is present in a proportion of 2 to 400 mg, preferably of 5 to 200 mg, and even more preferentially of 10 to 100 mg per unit form;
d) optionally, at least one quenching agent Q is contained in microparticles distinct from the microparticles of AP and of viscosity agent. The amount of agent Q is adjusted in order to trap all or part of the dose of AP contained in the unit form;

e) and, optionally, compression excipients.

According to an embodiment 7 of the invention, the tablet of embodiment 6 comprises at least one quenching agent Q.

As regards embodiments 6 and 7 of the invention, reference may be made to embodiments 1 to 5 of the invention to determine the nature of the components A1, A2, A3 and A4 of the coating layer R, that of the agent D, that of the viscosity agent V and, optionally, that of the quenching agent Q.

According to a preferred embodiment 8, the unit pharmaceutical form according to the invention is a gelatin capsule comprising:

a) an AP, at least part of which is contained in microparticles individually coated with a coating R which ensures the modified release of the AP and simultaneously confers resistance to crushing of the coated microparticles of AP.

For each constituent A1, A2, A3 and A4 of the coating layer R, its mass m (as % of the total mass A1+A2+A3+A4) bears out:

for A1: $10 \leq m \leq 90$, preferably $15 \leq m \leq 80$, and more preferentially $60 \leq m \leq 80$;

for A2: $2 \leq m \leq 50$, preferably $3 \leq m \leq 40$, and more preferentially $5 \leq m \leq 25$;

for A3: $1 \leq m \leq 30$, preferably $2 \leq m \leq 20$, and more preferentially $5 \leq m \leq 15$;

for A4: $0 \leq m \leq 40$, preferably $0 \leq m \leq 30$, and more preferentially $0 \leq m \leq 20$;

b) at least one agent D which is present in a proportion of 0.5% to 20% w/w, preferably of 0.5% to 15% w/w, and even more preferentially of 1% to 10% w/w, of the total mass of the unit form;

c) optionally, at least one viscosity agent V present in a proportion of 2 to 400 mg, preferably of 5 to 200 mg, and even more preferentially of 10 to 100 mg per unit form;

d) optionally, at least one quenching agent Q, the amount of which is adjusted in order to trap all or part of the dose of AP contained in the unit form.

According to an embodiment 9 of the invention, the gelatin capsule of embodiment 8 comprises at least one viscosity agent V.

According to an embodiment 10 of the invention, the gelatin capsule of embodiment 9 comprises at least one quenching agent Q.

Advantageously, the pharmaceutical form of gelatin capsule type comprises microparticles of viscosity agent V and/or microparticles of quenching agent Q, the microparticles of viscosity agent V and the microparticles of quenching agent Q being distinct from the microparticles of AP.

Preferably, the pharmaceutical form of gelatin capsule type comprises microparticles of AP, and also microparticles of viscosity agent V and/or microparticles of quenching agent Q, said microparticles having similar size distributions and similar densities and being impossible to separate from one another by sifting.

As regards embodiments 8, 9 and 10 of the invention, reference may be made to embodiments 1 to 5 of the invention to determine the nature of the components A1, A2, A3 and A4 of the coating layer R, that of the agent D, that of the viscosity agent V and, optionally, that of the quenching agent Q.

Active Principle

The AP used may belong, for example, to at least one of the families of following active substances: opiates, analgesics, antalgics, antitussives, anxiolytics, benzodiazepines, anorexigens, antidepressants, antiepileptics, antimigraine agents, antiparkinsonian agents, barbiturates, hypnotics, laxatives, neuroleptics, psychostimulants, psychotropic agents, sedatives, amphetamines, stimulants.

Even more specifically, the AP used is chosen from the following compounds: acetorphine, acetyl-alpha-methylfentanyl, acetyldihydrocodeine, acetylmethadol, alfentanil, allylprodine, alpha-cetylmethadol, alphameprodine, alphaprodine, alphamethadol, alpha-methylfentanyl, alpha-methylthiofentanyl, alphaprodine, anileridine, atropine, butorphanol, benzethidine, benzylmorphine, beta-hydroxyfentanyl, beta-hydroxymethyl-3-fentanyl, beta-cetylmethadol, betameprodine, betamethadol, betaprodine, bezitramide, buprenorphine, dioxaphetyl butyrate, clonitazene, cyclazocine, cannabis, cetobemidone, clonitazene, codeine, coca, cocaine, codoxime, dezocine, dimenoxadol, dioxaphetylbutyrate, dipipanone, desomorphine, dextromoramide, dextropropoxyphene, diampromide, diethylthiambutene, difenoxine, dihydrocodeine, dihydroetorphine, dihydromorphine, dimenoxadol, dimepheptanol, dimethylthiambutene, diphenoxylate, dipipanone, drotebanol, eptazocine, ethoheptazine, ethylmethylthiambutene, ethylmorphine, etonitazene, ecgonine, ephedrine, ethylmethylthiambutene, ethylmorphine, etonitazene, etorphine, etoxeridine, fentanyl, furethidine, heroin, hydrocodone, hydromorphinol, hydromorphone, hydroxypethidine, isomethadone, ketobemidone, levallorphan, lofentanil, levomethorphan, levomoramide, levophenacylmorphan, levorphanol, meptazinol, meperidine, metazocine, methadone, methyldesorphine, methyldihydromorphine, methylphenidate, methyl-3-thiofentanyl, methyl-3-fentanyl, metopon, moramide, morpheridine, morphine, myrophine, nalbuphine, narceine, nicomorphine, norlevorphanol, normethadone, nalorphine, normorphine, nicocodine, nicodicodine, nicomorphine, noracymethadol, norcodeine, norlevorphanol, normethadone, normorphine, norpipanone, opium, oxycodone, oxymorphone, papavereturn, phenadoxone, phenoperidine, promedol, properidine, propiram, propoxyphene, para-fluorofentanyl, pentazocine, pethidine, phenampromide, phenazocine, phenomorphan, phenoperidine, pholcodine, piminodine, piritramide, proheptazine, propranolol, properidine, propiram, racemethorphan, racemoramide, racemorphan, remifentanil, sufentanil, thebacone, thebaine, thiofentanyl, tilidine, trimeperidine, tramadol, and the pharmacologically acceptable salts, esters, hydrates, polymorphs and isomers thereof, and mixtures thereof.

Even more specifically, the analgesic AP used is selected from the group consisting of oxycodone hydrochloride, morphine sulfate, oxymorphone hydrochloride, hydromorphone hydrochloride, hydrocodone hydrochloride and tramadol hydrochloride.

For the purpose of the invention, the expression "pharmaceutical formulation" is understood in the broad sense, i.e. veterinary or dietetic formulations in particular are encompassed.

According to another of its aspects, the invention is directed toward a formulation which comprises a plurality of microparticles (of AP, coated or uncoated; optionally, of viscosity agent) as defined above, for example at least 500, preferably from 1000 to 1 000 000, and even more preferentially from 5000 to 500 000 microparticles.

According to another of its aspects, the invention is directed toward a pharmaceutical formulation comprising a plurality of populations of coated microparticles of AP, said populations differing from one another by virtue of their release kinetics and/or by virtue of the AP that they contain.

Advantageously, the pharmaceutical form according to the invention can comprise modified-release microparticles of AP and immediate-release microparticles of AP.

Without washing to be limiting, it should nevertheless be underlined that the pharmaceutical formulation according to the invention is particularly advantageous in that it can be in the form of a single oral daily dose comprising from 500 to 500 000 microparticles, including the coated microparticles of AP.

Without it being limiting, the pharmaceutical formulation comprising coated microparticles according to the invention is in a pharmaceutical form chosen from the group comprising in particular: tablets (advantageously orodispersible or gastrodispersible), powders, suspensions, syrups, powders for suspensions to be reconstituted, or gelatin capsules.

It may be advantageous to mix, in the same gelatin capsule, the same tablet or the same powder, at least two types of coated microparticles of AP having different release kinetics but included in the characteristic scope of the invention.

According to one variant, the pharmaceutical form can also be a monolithic form (for example, tablet).

According to a first variant, the pharmaceutical form according to the invention cannot be converted easily into a dry form that can be administered by nasal aspiration and with immediate release of AP.

According to a second variant, the pharmaceutical form according to the invention cannot be converted into an injectable form with immediate release of AP.

According to a third variant, the pharmaceutical form according to the invention comprises modified-release AP and, optionally, immediate-release AP. This variant can be combined with the first and second variants mentioned above. This means that, in a pharmaceutical form which comprises modified-release AP and immediate-release AP, the modified-release AP cannot be converted into a dry form that can be administered by nasal aspiration or into an injectable form, and with immediate release.

A subject of the present invention is also the methods for obtaining the pharmaceutical forms according to the invention as defined above, said methods being divided up into several steps consisting essentially in:

a) preparing uncoated microparticles of AP by:
   extrusion/spheronization of AP with, optionally, one or more agent(s) D or pharmaceutically acceptable excipient(s), and/or;
   wet granulation of AP with, optionally, one or more agent(s) D or pharmaceutically acceptable excipient(s), and/or;
   compacting of AP with, optionally, one or more agent(s) D or pharmaceutically acceptable excipient(s), and/or;
   spraying of AP, with, optionally, one or more agent(s) D or pharmaceutically acceptable excipient(s), in a dispersion or in a solution in an aqueous or organic solvent, onto a neutral support or particles of agent D, and/or;
   sifting of powder or crystals of AP;
b) preparing reservoir microparticles of AP by:
   spraying, in a fluidized air bed, of a solution or dispersion containing one or more compounds A1, A2 and A3 and, optionally, one or more compounds A4 and/or D, onto the microparticles of AP; the microparticles of AP may have been coated beforehand with one or more agents D; the coated microparticles of AP can optionally be coated with one or more agents D;
c) preparing the final form of the drug by:
   granulation and/or extrusion/spheronization of the reservoir microparticles of AP with agents D, V and Q for formulation in gelatin capsules or sachets; or
   mixing of reservoir microparticles of AP with, optionally, one or more agent(s) D, V and Q and pharmaceutically acceptable excipients, so as to obtain a tablet; this tablet can optionally be coated in a coating drum with one or more layers containing the agent D and/or pharmaceutically acceptable excipients; or
   formulation in gelatin capsules, of reservoir microparticles of AP, of V and of Q; the gelatin capsules can optionally be coated in a drum or fluidized air bed with one or more agent(s) D and/or pharmaceutically acceptable excipients; or
   formulation in sachets, of reservoir microparticles of AP, of V and of Q with, optionally, one or more agent(s) D and/or pharmaceutically acceptable excipients.

The invention also relates to a method of treating pain, comprising the administration of a pharmaceutical form as described above, to a patient needing the latter.

The invention also relates to a method for preventing misuse of an active principle, in particular analgesic or opiate, comprising the use of a pharmaceutical form as described above.

The invention will be explained more clearly by the examples hereinafter, which are given only by way of illustration and make it possible to clearly understand the invention and to reveal the variants of preparation and/or of use thereof, and also the various advantages thereof.

EXAMPLES

Example 1

Preparation According to the Invention of Anti-Crushing Microparticles of Oxycodone HCl Granules:
1615 g of oxycodone HCl are added to a solution containing 85 g of Methocel E5 (hypromellose/Dow), 2052 g of demineralized water and 1105 g of ethanol. The mixture is stirred at 67° C. The solution is then sprayed, in a Glatt GPCG 1.1 fluidized air bed device, onto 300 g of particles of Xantural 180 (xanthan gum/Danisco) sifted between 50 and 180 µm. The product recovered is then sifted through 80-300 µm.

Microparticles:
495 g of the granules prepared above are then film-coated, in a Glatt GPCG 1.1 fluidized air bed device, with a solution containing 296 g of Ethocel 20 Premium (ethylcellulose/Dow), 24 g of Plasdone K29/32 (povidone/ISP), 49 g of Cremophor RH 40 (PEG 40-hydrogenated castor oil/BASF), 41 g of castor oil (Garbit huilerie), 2795 g of acetone and 1863 g of isopropanol.

The mass of the coating represents 45% of the total mass of the MR microparticle of oxycodone HCl.

Example 2

Pharmaceutical Form According to Unpublished Application FR0553437

55 g of microparticles prepared in Example 1 are mixed with 18 g of Polyox WSR303 (polyethylene oxide/Dow) sifted between 150 and 300 µm, 26 g of Amberlite IR69F (Rhom & Haas) crushed and sifted between 160 and 300 µm, 0.5 g of Aerosil 200 (colloidal silica/Degussa) and 1 g of magnesium stearate.

405 mg of this mixture are introduced into gelatin capsules size 0.

This gelatin capsule is placed in a large volume (500 ml) of solution containing 40% of ethanol and the percentage released after stirring for 0.5 and 1 hour is measured:

| Time (h) | Oxycodone released (%) |
|---|---|
| 0.5 | 19 |
| 1 | 60 |

These results show that, in the presence of a large amount of alcoholic solution, the amount of oxycodone released is relatively high after one hour. This may present a risk for the patient, which is why the applicant has sought to develop a form with a slower release in the presence of alcohol.

Example 3

Crushing Test on the Microparticles of Oxycodone HCl

The microparticles prepared in Example 1 are lubricated with 1.0% of magnesium stearate and 0.5% of Aerosil.

These microparticles, in a proportion of 197 mg corresponding to a dose of 80 mg of oxycodone HCl, are introduced into a dissolutest, either as they are (INTACT), or highly crushed for 2 min by means of a pestle and mortar (CRUSHED).

The results of the dissolution test in 900 ml of 0.1N HCl (D as %) as a function of time (t in h) of the intact and crushed doses are reported in FIG. 1. The dissolution profiles are very similar, with a slightly more rapid release during the first minutes in the case of the crushed microparticles; subsequently, the profiles are similar.

Example 4

Preparation of Gelatin Capsules According to the Invention

Mixing:
55 g of microparticles prepared in Example 1 are mixed with 18 g of Polyox WSR303 (polyethylene oxide/Dow) sifted between 150 and 300 μm, 26 g of Amberlite IR69F (Rhom & Haas) crushed and sifted between 160 and 300 μm, 0.5 g of Aerosil 200 (colloidal silica/Degussa) and 1 g of magnesium stearate. The mixture is homogenized for 15 minutes.

Gelatin Capsules:
35 gelatin capsules size 0 (white/white) are each filled with 405 mg of the mixture above.

Coating of the Gelatin Capsules:
The gelatin capsules above are then coated with 16 mg per gelatin capsule of Blanose 7LF (sodium carboxymethylcellulose/Aqualon) dissolved beforehand at 6% (m/m) in demineralized water.

Figure 2:
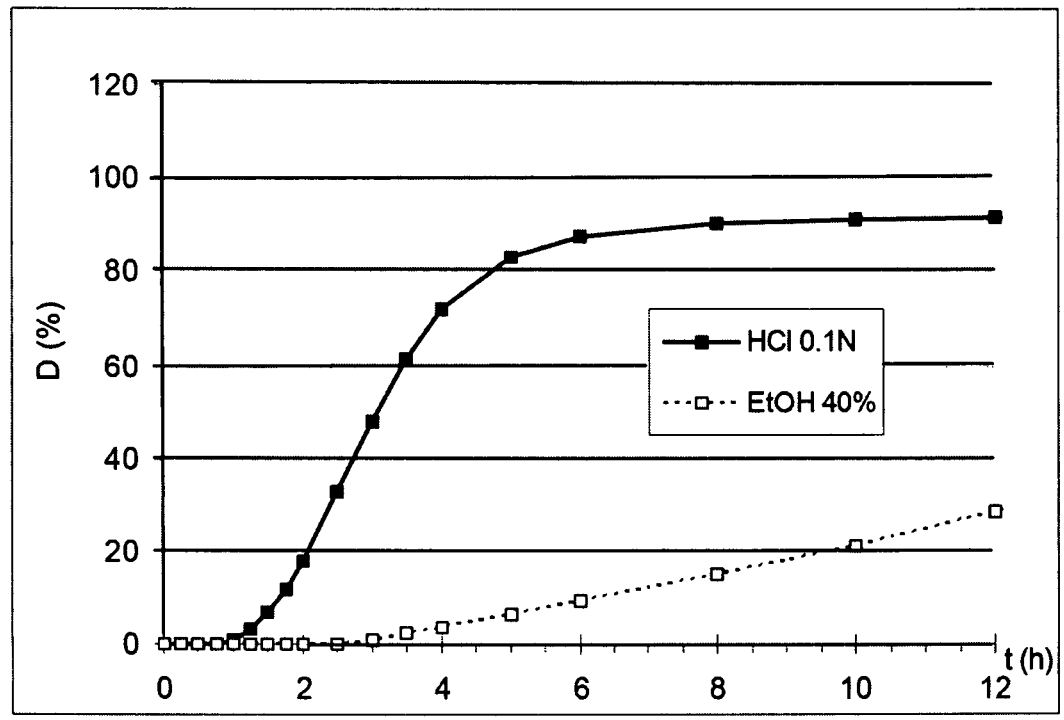
FIG. 2: dissolution of the gelatin capsules prepared in example 4
□: in 40% EtOH ■: in 0.1N HCl

The dissolution tests in 900 ml of 0.1N HCl and (40% EtOH; 60% 0.1N HCl) are reported in FIG. 2. It is noted that, in an ethanolic solution, the dissolution kinetics are considerably slowed.

Example 5

Misuse Test on the Content of the Gelatin Capsule of Example 4

In the following misuse tests, the content of a gelatin capsule as described in Example 4 is first crushed by means of a pill crusher (LGS pill crusher) and then brought into contact with 10 ml of solvent and left stirring for 120 min at ambient temperature.

The mixture is then removed by means of an insulin syringe through a 0.45 μm filter. The amounts of oxycodone HCl recovered are analyzed by HPLC. The results of the extraction tests are reported in Table 1.

TABLE 1

| Solvent | Oxycodone extracted (%) |
|---|---|
| 70% Isopropanol | 0 |
| Diethyl ether | 0.02 |
| Ethyl acetate | 1.9 |
| Ethanol | 13.7 |
| Acetone | 1.1 |
| Cooking oil | <0.01 |

The amounts extracted are less than 15% of the dose.

Example 6

Preparation of Tablets According to the Invention 10 g of the microparticles of oxycodone prepared in Example 1, 5 g of Amberlite IR69F (Rhom & Haas) sifted between 160 and 300 μm, 2.5 g of Polyox WSR 303, 10 g of Avicel PH 101 (microcrystalline cellulose/FMC), 5 g of Methocel A15 (methylcellulose/Dow) and 0.25 g of magnesium stearate are mixed and then tableted. The mass of the tablets is 655 mg.

Figure 3:
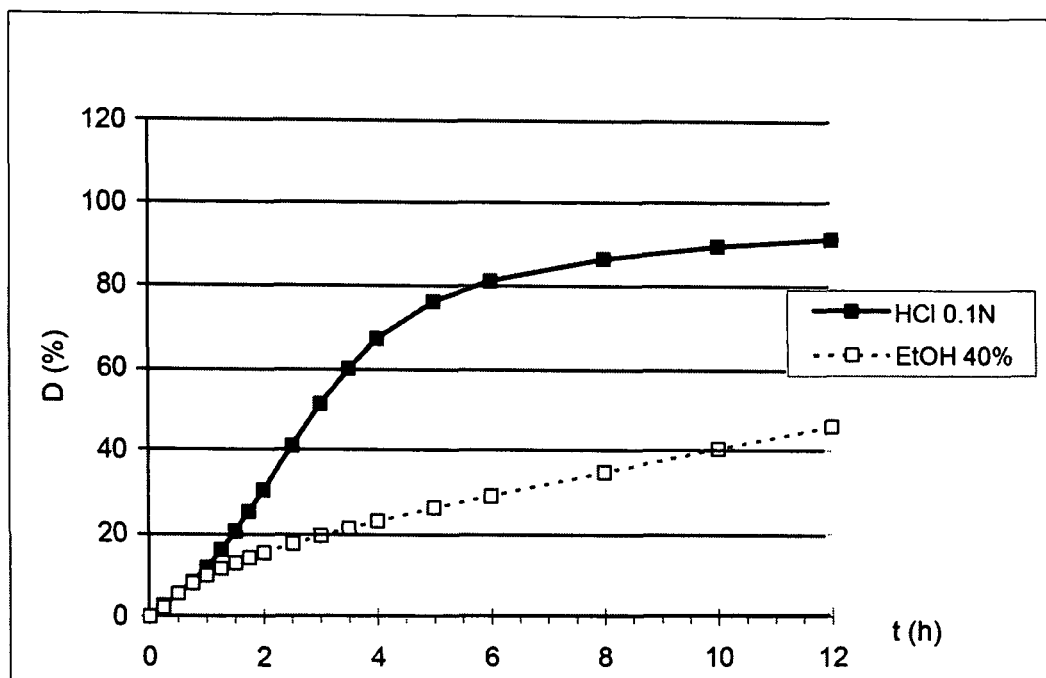
FIG. 3: dissolution of the tablets prepared in example 6
□: in 40% EtOH ■: in 0.1N HCl

The tests for dissolution of these tablets in 900 ml of 0.1N HCl and (40% EtOH; 60% 0.1N HCl) are reported in FIG. 3. It is noted that the release in an alcoholic medium is slower than in an aqueous medium.

Example 7

Preparation According to the Invention of Anti-Crushing Microparticles of Oxycodone HCl Granules:
1582.7 g of oxycodone HCl are added to a solution containing 83.3 g of Plasdone K29/32 (povidone/Dow), 2011.1 g of demineralized water and 1082.9 g of ethanol. The mixture is stirred at 67° C. The solution is then sprayed, in a Glatt GPCG 1.1 fluidized air bed device, onto 300 g of particles of cellulose spheres (Asahi-Kasei). The product recovered is then sifted on 80-300 μm.

Microparticles:
450 g of the granules prepared as indicated above are then film-coated, in a Glatt GPCG 1.1 fluidized air bed device, with a solution containing 315 g of Ethocel 20 Premium (ethylcellulose/Dow), 36 g of Plasdone K29/32 (povidone/ISP), 54 g of Lutrol F-68 (Poloxamer 188/BASF), 45 g of castor oil (*Garbit huilerie*), 3105 g of acetone and 2070 g of isopropanol. The mass of the coating represents 50% of the total mass of the MR microparticle of oxycodone HCl.

Example 8

Preparation of Tablets According to the Invention 11 g of microparticles of oxycodone prepared in Example 7, 4 g of Amberlite IR69F (Rhom & Haas) sifted between 160 and 300 μm, 2 g of Polyox WSR 303, 8 g of talc (Iuzenac 00), 4 g of Methocel A15 (methylcellulose/Dow) and 0.5 g of magnesium stearate are mixed and then tableted. The mass of the tablets is 590 mg.

Figure 4:
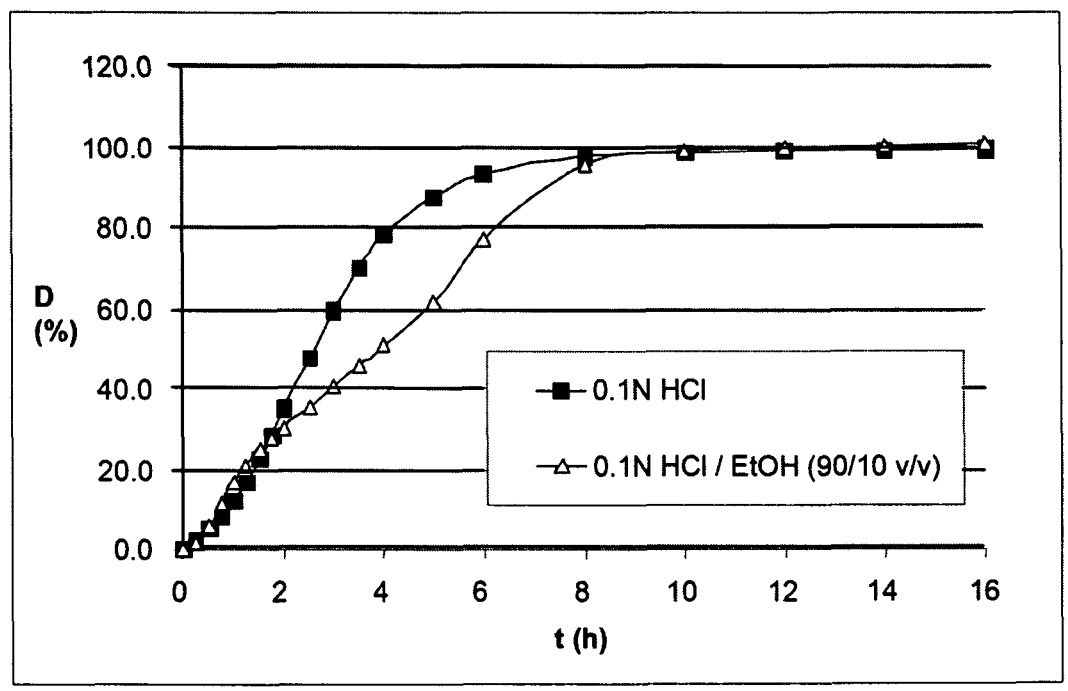
FIG. 4: dissolution of the tablets prepared in example 8
■: in 0.1N HCl ∆: in 0.1N HCl/EtOH (90/10 v/v)

The tests for dissolution of these tablets in 900 ml of 0.1N HCl and (10% EtOH; 90% 0.1N HCl) are reported in FIG. 4. The rate of release in a medium containing 10% of ethanol is comparable to or even slower than that obtained in a purely aqueous medium.

Example 9

Preparation of Tablets According to the Invention 11 g of microparticles of oxycodone prepared in Example 7, 4 g of Amberlite IR69F (Rhom & Haas) crushed and sifted between 160 and 300 μm, 2 g of polyethylene oxide (Polyox WSR 303/Sentry), 5 g of talc (Luzenac 00), 2 g of methylcellulose (Methocel A15/Dow), 2 g of hydroxyethylcellulose (Natrosol 250G/Aqualon), 3 g of microcrystalline cellulose (Avicel PH200/FMC) and 0.5 g of magnesium stearate are mixed and then tableted. The mass of the tablets is 590 mg.

Figure 5:
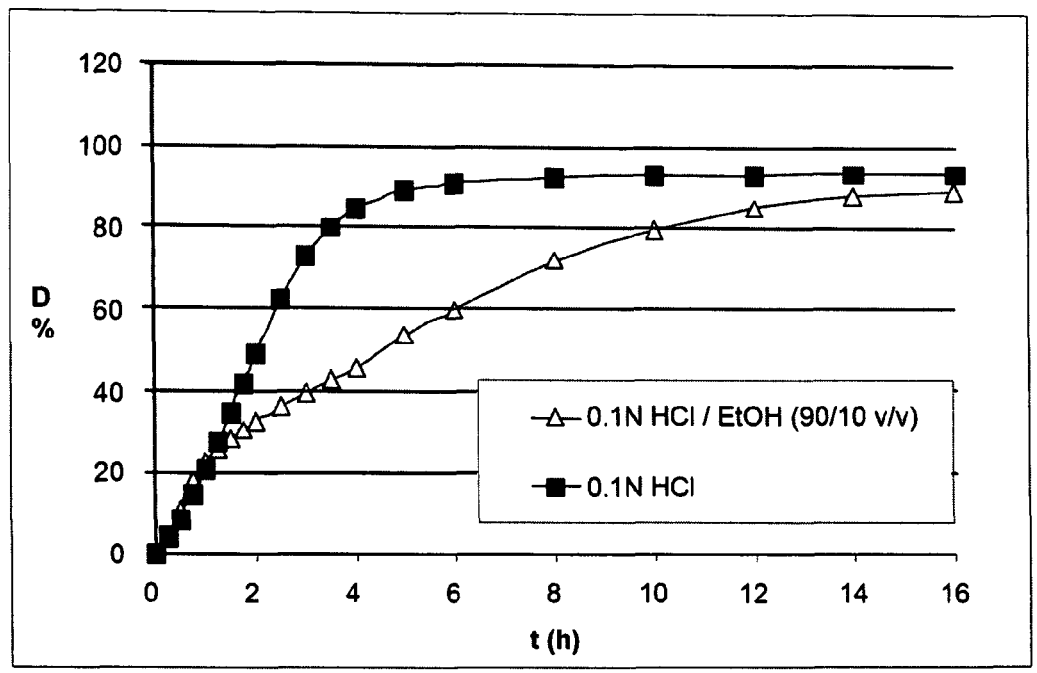
FIG. 5: dissolution of the tablets prepared in example 9
■: in 0.1N HCl ∆: in 0.1N HCl/EtOH (90/10 v/v)

The tests for dissolution of these tablets in 900 ml of 0.1N HCl and (10% EtOH; 90% 0.1N HCl) are reported in FIG. 5. The rate of release in a medium containing 10% of ethanol is comparable to or even slower than that obtained in a purely aqueous medium.

Example 10

Preparation of Tablets According to the Invention 10 g of microparticles of oxycodone prepared in Example 1, 5 g of Amberlite IR69F (Rhom & Haas) crushed and sifted between 160 and 300 μm, 2.5 g of polyethylene oxide (Polyox WSR 303/Sentry), 10 g of microcrystalline cellulose (Avicel PH101/FMC), 2.5 g of hypromellose (Methocel E15/Dow), 2.5 g of hypromellose (Methocel E5/Dow), and 0.25 g of magnesium stearate are mixed and then tableted. The mass of the tablets is 655 mg.

Figure 6:
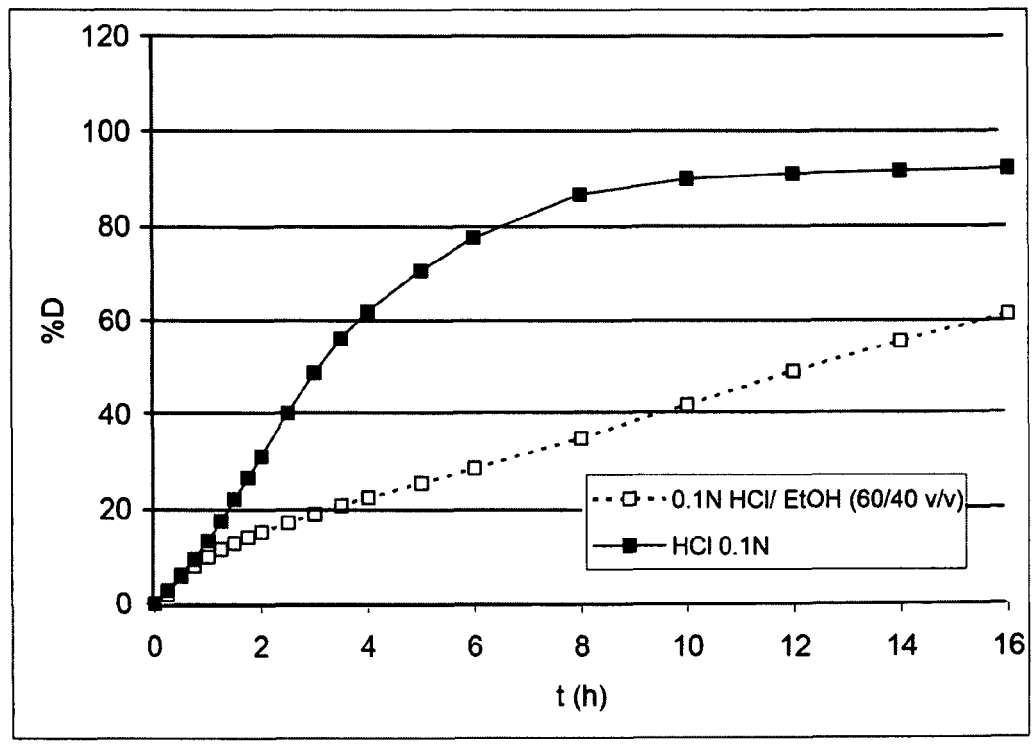
FIG. 6: dissolution of the tablets prepared in example 10
■: in 0.1N HCl □: in 0.1N HCl/EtOH (60/40 v/v)

The tests for dissolution of these tablets in 900 ml of 0.1N HCl and (40% EtOH; 60% 0.1N HCl) are reported in FIG. 6.

Example 11

Preparation According to the Invention of Anti-Crushing Microparticles of Oxycodone HCl Granules:
1615 g of oxycodone HCl are added to a solution containing 85 g of povidone (Plasdone K29/32/ISP), 2052 g of demineralized water and 1105 g of ethanol. The mixture is stirred at 67° C. The solution is then sprayed, in a Glatt GPCG 1.1 fluidized air bed device, onto 300 g of particles of cellulose spheres (Cellets 90/Pharmatrans). The product recovered is then sifted on 80-250 μm.

Microparticles:
450 g of the granules prepared as indicated above are then film-coated, in a Glatt GPCG 1.1 fluidized air bed device, with a solution containing 315 g of ethylcellulose (Ethocel 20 Premium/Dow), 54 g of povidone (Plasdone K29/32/ISP), 27 g of PEG40 hydrogenated castor oil (Cremophor RH 40/BASF), 54 g of castor oil (*Garbit huilerie*), 3105 g of acetone and 2070 g of isopropanol. The mass of the coating represents 50% of the total mass of the MR microparticle of oxycodone HCl.

Example 12

Preparation of Tablets According to the Invention 55 mg of microparticles of oxycodone prepared in Example 11, 20 mg of Amberlite IR69F (Rhom & Haas) sifted between 160 and 300 μm, 40 mg of polyethylene oxide (Polyox WSR 303/Sentry), 120 mg of microcrystalline cellulose (Avicel PH301/FMC), 10 mg of methylcellulose (Methocel A15LV/Dow), 5 mg of hydroxypropylcellulose (Klucel HXF/Aqualon), 5 mg of magnesium stearate, 185 mg of mannitol (Pearlitol SD200/Roquette) and 25 mg of sodium bicarbonate (Merck) are mixed and then tableted with a Korsch XP-1 press.

Figure 7:
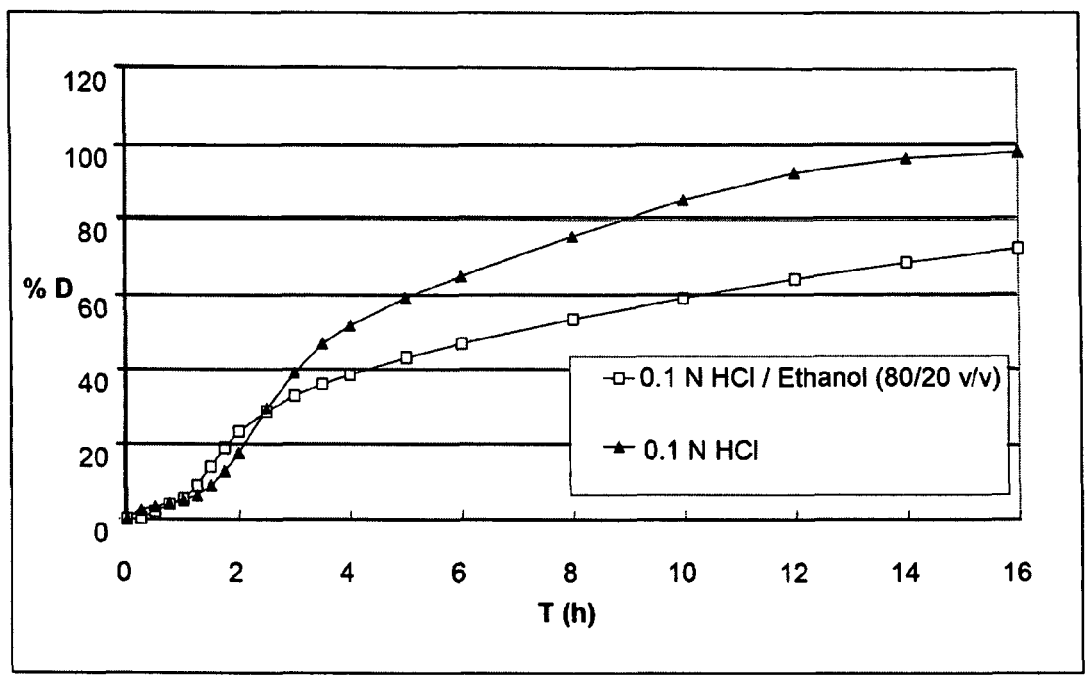
FIG. 7: dissolution of the tablets prepared in example 12
▲: in 0.1N HCl □: in 0.1N HCl/EtOH (80/20 v/v)
EtOH denotes ethanol.

These tablets have a slower release kinetics in a 20% v/v ethanol medium than in a 0.1N HCl medium (FIG. 7).

What is claimed is:

1. An oral pharmaceutical form resisting dose dumping in the presence of alcohol, wherein said pharmaceutical form comprises:
   i) coated microparticles comprising at least active principle (AP) and providing modified release of said AP;
   ii) at least one viscosity agent V; and
   iii) an agent D selected from the group consisting of: methylcellulose: hydroxypropylmethylcellulose, hydroxypropylcellulose, hydroxyethylcellulose, carboxy(alkyl)celluloses and salts thereof, and mixture thereof;
   wherein said AP is selected from the group consisting of: opiates, anxiolytics, benzodiazepines, anorexigens, antidepressants, antiepileptics, antiparkinsonian agents, barbiturates, hypnotics, neuroleptics, psychostimulants, psychotropic agents, amphetamines and mixtures thereof;
   wherein the coated microparticles of AP comprise a coating layer R;
   wherein said coating layer R ensures the modified release of the AP and simultaneously confers, on the coated microparticles of AP, resistance to crushing;
   wherein said coating layer R represents 30-60% of the total mass of the coated microparticles of AP;
   wherein said coating layer R comprises:
      at least one film-forming (co)polymer A1 which is insoluble in the fluids of the digestive tube, representing between 60% and 90% by weight relative to the weight of the coating layer R;
      at least one (co)polymer A2 which is soluble in the fluids of the digestive tubes, representing between 5% and 40% by weight relative to the weight of the coating layer R; and
      at least one plasticizer A3, representing between 1% and 30% by weight relative to the weight of the coating layer R;
   wherein the viscosity agent V is in the form of microparticles distinct from the microparticles of AP,
   wherein the agent D is present in a mixture with the coated microparticles of AP, in the form of microparticles distinct from the microparticles of AP, or is one of the outer constituents of a monolithic form.

2. The pharmaceutical form of claim 1, further comprising at least one quenching agent Q in the form of microparticles distinct from the microparticles of AP.

3. The pharmaceutical form of claim 1, in which the agent D is present in the mixture with the coated microparticles of AP, in a proportion of 0.5% to 30% w/w of the total mass of the unit form.

4. The pharmaceutical form as claimed in claim 1, in which the coating layer R further comprises:

at least one surfactant and/or one lubricant and/or mineral filler and/or organic filler A4, representing less than 40% by weight relative to the weight of the coating layer R.

5. The pharmaceutical form as claimed in claim 1, in which:
A1 is selected from the group consisting of: water-insoluble derivatives of cellulose, acrylic polymers, poly(vinyl acetate)s, and mixtures thereof;
A2 is selected from the group consisting of: nitrogenous (co)polymers, water-soluble derivatives of cellulose, polyvinyl alcohols (PVAs), polyalkylene oxides, polyethylene glycols (PEGs), and mixtures thereof;
A3 is selected from the group consisting of: cetyl alcohol esters, glycerol and esters thereof, phthalates, citrates, sebacates, adipates, azelates, benzoates, plant oils, fumarates, malates, oxalates, succinates, butyrates, cetyl alcohol esters, malonates, castor oil and mixtures thereof.

6. The pharmaceutical form as claimed in claim 5, in which:
A1 is selected from the group consisting of water-insoluble derivatives of cellulose,
A2 is selected from the group consisting of: polyacrylamides, poly-N-vinylamides, polyvinylpyrrolidones (PVPs) and poly-N-vinyllactams, water-soluble derivatives of cellulose, polyethylene glycols (PEGs), and mixtures thereof;
A3 is selected from the group consisting of: triethyl citrate, dibutyl sebacate, plant oils, castor oil and mixtures thereof.

7. The pharmaceutical form of claim 1, wherein the coating layer (R) comprises A1, A2, and A3 in the following proportions (in % by weight, based on the total weight of the coating):
for A1: $60 \leq m \leq 80$,
for A2: $5 \leq m \leq 25$,
for A3: $5 \leq m \leq 15$.

8. The pharmaceutical form as claimed in claim 1, in which at least one viscosity agent V is chose from viscosity agents which are soluble in at least one of the following extraction solvents: water, alcohol, ketones, and mixtures thereof.

9. The pharmaceutical form as claimed in claim 1, in which the viscosity agent V is selected from the group consisting of: poly(meth)acrylic acid and poly(meth)acrylic-based compounds, polyalkylene glycols, or polyalkylene oxides, polyvinylpyrrolidones, gelatins, sodium alginate, pectins, guars, xanthans, carrageenans, gellans, hydroxypropylmethylcellulose, methylcellulose, hydroxyethylcellulose, hydroxypropylcellulose, carboxymethylcellulose and mixtures thereof.

10. The pharmaceutical form as claimed in claim 9, in which the viscosity agent V is selected from the group consisting of: polyalkylene oxides, xanthans, hydroxypropylcellulose, and mixtures thereof.

11. The pharmaceutical form of claim 8, in which the amount of agent V in the pharmaceutical form is adjusted so as to render the viscosity of 2.5 ml of the extraction solvent greater than or equal to 100 mPa·s.

12. The pharmaceutical form of claim 1, in which the viscosity agent V is a polyoxyethylene having a molecular weight of 1 million g/mol to 8 million g/mol.

13. The pharmaceutical form as claimed in claim 2, in which the quenching agent Q comprises a salt, which contains ions capable of forming a complex with salt of AP extracted in solution.

14. The pharmaceutical form as claimed in claim 13, in which the ions of the quenching Q are organic ions of polarity opposite to that of the AP in solution, and which form a complex with the salt of AP extracted in solution.

15. The pharmaceutical form of claim 13, in which the quenching agent Q is present in a first phase separate from at least a second phase, said second phase containing at least one salt of AP.

16. The pharmaceutical form as claimed in claim 2, in which microparticles of AP and microparticles of quenching agent Q have a similar size distribution and a similar density and are impossible to separate from one another by sifting.

17. The pharmaceutical form as claimed in claim 14, in which the ion of polarity opposite to that of the AP in solution is an organic anion.

18. The pharmaceutical form of claim 13, in which the quenching agent Q comprises a salt selected from the group consisting of: anionic organic salts, anionic polymers, monovalent or polyvalent salts, saponified fatty acids, polyamino acids, proteins, peptides, and mixtures thereof.

19. The pharmaceutical form as claimed in claim 13, in which the ion capable of forming a complex with salt of AP extracted in solution is a metal cation, an organic cation, or a mixture thereof.

20. The pharmaceutical form of claim 13, in which the quenching agent Q comprises a salt selected from the group consisting of: cationic salts, organic cationic salts, cationic polymers, polyamino acids, proteins, peptides; and mixtures thereof.

21. The pharmaceutical form of claim 13, in which the quenching agent Q is an ion exchange resin.

22. The pharmaceutical form as claimed in claim 21, in which the quenching agent Q is a derivative of a styrene/divinylbenzene copolymer.

23. The pharmaceutical form as claimed in claim 21, in which the quenching agent Q is a derivative of a sulfonic styrene/divinylbenzene copolymer.

24. The pharmaceutical form as claimed in claim 21, in which the quenching agent Q is a derivative of styrene/divinylbenzene copolymer bearing quaternary ammonium functions.

25. The pharmaceutical form as claimed in claim 21, in which the quenching agent is a crosslinked copolymer of methacrylic acid and of divinylbenzene, or a salt thereof.

26. The pharmaceutical form as claimed in claim 21, in which the ion exchange resin is a phenolic polyamine.

27. The pharmaceutical form claim 13, in which the quenching agent Q is chosen from: anionic organic salts, cationic organic salts and strongly acidic cation exchange resins or strongly basic anion exchange resins, depending on the polarity of the AP.

28. The pharmaceutical form of claim 13, in which the amount of quenching agent is adjusted so as to complex all or part of the dose of AP contained in the unit form.

29. The pharmaceutical form of claim 1, comprising at least one excipient not contained in or supported by the microparticles of AP, said excipient contributing to the resistance of crushing of the coated microparticles of AP and selected from the group consisting of calcium stearate, glyceryl behenate, glyceryl palmitostearate, magnesium oxide, polyalkylene glycols, polyvinyl alcohol, sodium benzoate, stearic acid, corn starch, talc, colloidal silica, zinc stearate, magnesium stearate, stearyl fumarate, and mixtures thereof.

30. The pharmaceutical form of claim 2, comprising:
a) an AP, at least part of which is contained in microparticles individually coated with a coating R which ensures the modified release of the AP and simultaneously confers resistance to crushing of the coated microparticles of AP, where for each constituent A1, A2 and A3 of the coating layer R, its mass m (as % of the total mass of the coating R) bears out:
for A1: 60≤m≤90,
for A2: 5≤m≤40,
for A3: 1≤m≤30,
b) at least one agent D which is present in a proportion of 0.5% to 30% w/w, of the total mass of the unit form;
c) at least one viscosity agent V present in a proportion of 2 to 400 mg,
d) at least one quenching agent Q, the amount of which is adjusted in order to trap all or part of the dose of AP contained in the unit form, the quenching agent Q being included in a separate phase distinct from the phase containing the AP.

31. The pharmaceutical form as claimed in claim 30, comprising microparticles of viscosity agent V and coated microparticles of AP, said microparticles having a similar size distribution and a similar density and being impossible to separate from one another by sifting.

32. The pharmaceutical form of claim 30, in which the coating layer R contains the following components:
A1 selected from the group consisting of:
water-insoluble derivatives of cellulose,
A2 selected from the group consisting of:
nitrogenous (co)polymers, water-soluble derivatives of cellulose, polyethylene glycols (PEGs), and mixtures thereof;
A3 selected from the group consisting of:
triethyl citrate, dibutyl sebacate, plant oils, castor oil, and mixtures thereof.

33. The pharmaceutical form of claim 30, in which the viscosity agent V is chosen from: polyalkylene oxides, xanthans, cellulose derivatives and mixtures thereof.

34. The pharmaceutical form of claim 30, in which the quenching agent Q is selected from the group consisting of: anionic organic salts, cationic organic salts and ion exchange resins.

35. The pharmaceutical form of claim 30, in which the quenching agent Q is chosen from: strongly acidic cation exchange resins and mixtures thereof, when the AP is cationic; strongly basic anion exchange resins and mixtures thereof, when the AP is anionic.

36. The pharmaceutical form of claim 30, which is in a tablet form, comprising:
a) an AP, at least part of which is contained in microparticles individually coated with a coating R which ensures the modified release of the AP and simultaneously confers resistance to crushing of the coated microparticles of AP, where, for each constituent A1, A2 and A3 of the coating layer R, its mass m (as % of the total mass of the coating R) bears out:
for A1: 60≤m≤90,
for A2: 5≤m≤40,
for A3: 1≤m≤30,
b) at least one agent D is present as a mixture with the microparticles in a proportion of 1% to 30% w/w of the total mass of the unit form;
c) at least one viscosity agent V contained in microparticles distinct from the microparticles of AP, in a proportion of 2 to 400 mg-per unit form;
d) at least one quenching agent Q contained in microparticles distinct from the microparticles of AP and of viscosity agent; the amount of quenching agent being adjusted in terms of ionic charge, in order to trap all or part of the dose of AP contained in the unit form;
e) compression excipients.

37. The pharmaceutical form of claim 30, which is in a gelatin capsule unit form, comprising:
a) an AP, at least part of which is contained in microparticles individually coated with a coating R which ensures the modified release of the AP and simultaneously confers resistance to crushing of the coated microparticles of AP, and where, for each constituent A1, A2 and A3 of the coating layer R, its mass m (as % of the total mass of the coating R) bears out:
for A1: 60≤m≤90,
for A2: 5≤m≤40,
for A3: 1≤m≤30,
b) at least one agent D which is present in a proportion of 0.5% to 20% w/w, of the total mass of the unit form;
c) at least one viscosity agent V contained in microparticles distinct form the microparticles of AP, in a proportion of 2 to 400 mg, per unit form;
d) at least one quenching agent Q contained in microparticles distinct from the microparticles of AP and of viscosity agent; the amount of quenching agent being adjusted in terms of ionic charge, in order to trap all or part of the dose of AP contained in the unit form.

38. The pharmaceutical form of claim 37, comprising coated microparticles of AP, and also microparticles of viscosity agent V and/or microparticles of quenching agent Q, said microparticles having a similar size distribution and a similar density and being impossible to separate form one another by sifting.

39. The pharmaceutical form of claim 1, wherein the coated microparticles of AP have a volume-average diameter of less than or equal to 1000 μm.

40. The pharmaceutical form of claim 1, comprising at least:
microparticles of AP coated with a coating and resistant to crushing; an ion exchange resin;
polyoxyethylene; methylcellulose.

41. The pharmaceutical form of claim 1, comprising at least: microparticles of AP coated with a coating and resistant to crushing; an ion exchange resin; polyoxyethylene; methylcellulose; hydroxyethylcellulose.

42. The pharmaceutical form as claimed in claim 37, which is in the form of a gelatin capsule coated with an agent D based on sodium carboxymethylcellulose.

43. The pharmaceutical form as claimed in claim 37, which is in the form of a gelatin capsule coated with an agent D based on hydroxyethylcellulose.

44. The pharmaceutical form of claim 1, comprising modified-release microparticles of AP and immediate-release microparticles of AP.

45. The pharmaceutical form of claim 1, comprising a plurality of populations of coated microparticles of AP, said populations differing from one another by virtue of their release kinetics and/or by virtue of the AP that they contain.

46. The pharmaceutical form claim 1, in which the active principle is chosen from the group consisting of: acetorphine, acetyl-alpha-methylfentanyl, acetyldihydrocodeine, acetylmethadol, alfentanil, allylprodine, alpha-cetylmethadol, alphameprodine, alphaprodine, alphamethadol, alpha-methylfentanyl, alphamethylthiofentanyl, anileridine, butorphanol, benzethidine, benzylmorphine, beta-hydroxyfentanyl, beta-hydroxymethyl-3-fentanyl, beta-cetylmethadol, betameprodine, betamethadol, betaprodine, bezitramide, buprenorphine, dioxaphetyl butyrate, clonitazene, cyclazocine, cannabis, codeine, coca, cocaine, codoxime, dezocine, dimenoxadol, dipipanone, desomorphine, dextromoramide, dextropropoxyphene, diampromide, diethylthiambutene, difenoxin, dihydrocodeine, dihydroetorphine, dihydromorphine, dimenoxadol, dimepheptanol, dimethylthiambutene, diphenoxylate, dipipanone, drotebanol, eptazocine, ethoheptazine, ethylmethylthiambutene, ethylmorphine, etonitazene, ethylmethylthiambutene, ethylmorphine, etorphine, etoxeridine, fentanyl, furethidine, heroin, hydrocodone, hydromorphinol, hydromorphone, hydroxypethidine, isomethadone, ketobemidone, levallorphan, lofentanil, levomethorphan, levomoramide, levophenacylmorphan, levorphanol, meptazinol, meperidine, metazocine, methadone, methyldesorphine, methyldihydromorphine, methylphenidate, methyl-3-thiofentanyl, methyl-3-fentanyl, metopon, moramide, morpheridine, morphine, myrophine, nalbuphine, narceine, norlevorphanol, normethadone, nalorphine, normorphine, nicocodine, nicodicodine, nicomorphine, noracymethadol, norcodeine, norpipanone, opium, oxycodone, oxymorphone, papaveretum, phenadoxone, phenoperidine, promedol, properidine, propiram, propoxyphene, parafluorofentanyl, pentazocine, pethidine, phenampromide, phenazocine, phenomorphan, phenoperidine, pholcodine, piminodine, piritramide, proheptazine, racemethorphan, racemoramide, racemorphan, remifentanil, sufentanil, thebacone, thebaine, thiofentanyl, tilidine, trimeperidine, tramadol, and the pharmacologically acceptable salts, esters, hydrates, polymorphs and isomers thereof, and mixtures thereof.

47. The pharmaceutical form of claim 1, in which the AP is selected from the group consisting of oxycodone hydrochloride, morphine sulfate, oxymorphone hydrochloride, hydromorphone hydrochloride, hydrocodone hydrochloride and tramadol hydrochloride.

48. A method for obtaining a pharmaceutical form of claim 1, in several steps comprising:
   a) preparing uncoated microparticles of AP by:
      extrusion/spheronization of AP;
      wet granulation of AP;
      compacting of AP;
      spraying of AP, onto a neutral support or;
      sifting of powder or crystals of AP;
   b) preparing reservoir microparticles of AP by:
      spraying, in a fluidized air bed, a solution or dispersion containing A1, A2 and A3 onto the uncoated microparticles of AP;
   c) preparing the final form of the drug by:
      granulation or extrusion/spheronization of the reservoir microparticles of AP with agents D, V and Q for formulation in gelatin capsules or sachets;
      mixing of reservoir microparticles of AP with one or more agent(s) D, V and Q and pharmaceutically acceptable excipients, so as to obtain a tablet;
      formulation in gelatin capsules, of reservoir microparticles of AP, of V and of Q, wherein said gelatin capsules are coated with one or more agent(s) D; or
      formulation in sachets, of reservoir microparticles of AP, of V and of Q with one or more agent(s) D and pharmaceutically acceptable excipients.

49. The pharmaceutical form of claim 1, wherein the coating layer R represents a fraction by mass Tp, expressed as a percentage by weight on a dry basis relative to the total weight of the microcapsules, is between 40-60%.

50. The pharmaceutical form of claim 1, wherein the coating layer R represents a fraction by mass Tp, expressed as a percentage by weight on a dry basis relative to the total weight of the microcapsules, is between 45-55%.

51. The pharmaceutical form as claimed in claim 4, wherein the coating layer R further comprises less than 40% by weight of A4 relative to the weight of the coating layer R, wherein A4 is selected from the group consisting of: polyoxyethylenated oils, polyethylene oxide-polypropylene oxide copolymers (poloxamer), polyoxyethylenated sorbitan esters, polysorbates, stearates, and mixtures thereof.

52. The pharmaceutical form as claimed in claim 4, in which A4 is selected from the group consisting of: anionic surfactants, nonionic surfactants, stearates, stearyl fumarates, glycerol behenates, talc, colloidal silica, titanium oxide, magnesium oxide, bentonite, microcrystalline cellulose, kaoline, aluminum silicate, and mixtures thereof.

53. The pharmaceutical form as claimed in claim 52, in which A4 is selected from the group consisting of: anionic surfactants.

54. The pharmaceutical form of claim 4, in which A4 represents less than 20% by weight relative to the weight of the coating layer R.

55. The pharmaceutical form of claim 1, wherein said core comprising said AP is a matrix granule containing said AP and other pharmaceutically acceptable excipients or is a neutral support particle coated with at least one layer comprising said AP.

* * * * *